(12) United States Patent
Fujita et al.

(10) Patent No.: US 6,342,335 B1
(45) Date of Patent: Jan. 29, 2002

(54) POLYMETHINE COMPOUNDS, METHOD OF PRODUCING SAME, AND USE THEREOF

(75) Inventors: Shigeo Fujita, Osaka; Nobuaki Sasaki; Keiki Chichiishi, both of Kyoto; Yasuhisa Iwasaki, Nara, all of (JP)

(73) Assignee: Yamamoto Chemicals, Inc., Osaka (JP)

( * ) Notice: Subject to any disclaimer, the term of this patent is extended or adjusted under 35 U.S.C. 154(b) by 0 days.

(21) Appl. No.: 09/598,044

(22) Filed: Jun. 20, 2000

(30) Foreign Application Priority Data

Jun. 21, 1999 (JP) .......................................... 11-174235

(51) Int. Cl.[7] ................................................ G03F 7/00

(52) U.S. Cl. .................... 430/270.1; 430/302; 430/944; 430/945; 101/463.1; 101/453; 548/469

(58) Field of Search ............................. 430/270.1, 302, 430/944, 945, 270.11, 270.21; 101/453, 463.1; 548/469

(56) References Cited

U.S. PATENT DOCUMENTS

| | | | |
|---|---|---|---|
| 4,973,572 A | * 11/1990 | DeBoer | 503/227 |
| 4,987,021 A | * 1/1991 | Kanno et al. | 428/64 |
| 5,814,431 A | * 9/1998 | Nagasaka et al. | 430/281.1 |

FOREIGN PATENT DOCUMENTS

| | | |
|---|---|---|
| EP | 1063231 A1 | * 12/2000 |
| JP | 62-187091 A | * 8/1987 |
| JP | 62-207685 A | * 9/1987 |
| JP | 62-082080 A | * 4/1997 |

OTHER PUBLICATIONS

Narayanan, Narasimhachari and Gabor Patonay. "A New Method for the Synthesis of Heptamethine Cyanine Dyes: Synthesis of New Near–Infrared Fluorescent Labels." J. Org. Chem. 60 (1995): 2391–2395.*

* cited by examiner

*Primary Examiner*—Janet Baxter
*Assistant Examiner*—Barbara Gilmore
(74) *Attorney, Agent, or Firm*—Birch, Stewart, Kolasch & Birch, LLP

(57) ABSTRACT

The invention provides near infrared absorbing materials showing high light-to-heat conversion efficiency and high sensitivity to lasers whose emission bands are within the range of 750 nm to 900 nm, original plates for direct printing plate making, and novel compounds which can be applied to such absorbing materials and plates. The compounds are polymethine compounds of the general formula (I) A detailed description of general formula (I) may be found in the specification.

(I)

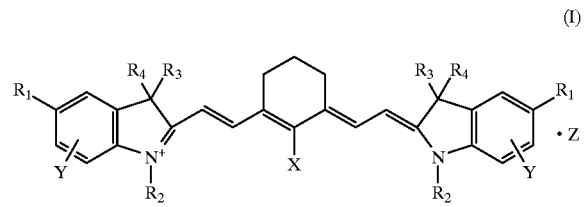

wherein $R_1$ represents an alkoxy group which may be substituted; $R_2$ represents an alkyl group which may be substituted; $R_3$ and $R_4$ each represents a lower alkyl group or $R_3$ and $R_4$ taken together represent a ring; X represents a hydrogen atom, a halogen atom or a substituted amino group; Y represents an alkoxy group which may be substituted or an alkyl group which may be substituted; Z represents a charge neutralizing ion.

15 Claims, 15 Drawing Sheets

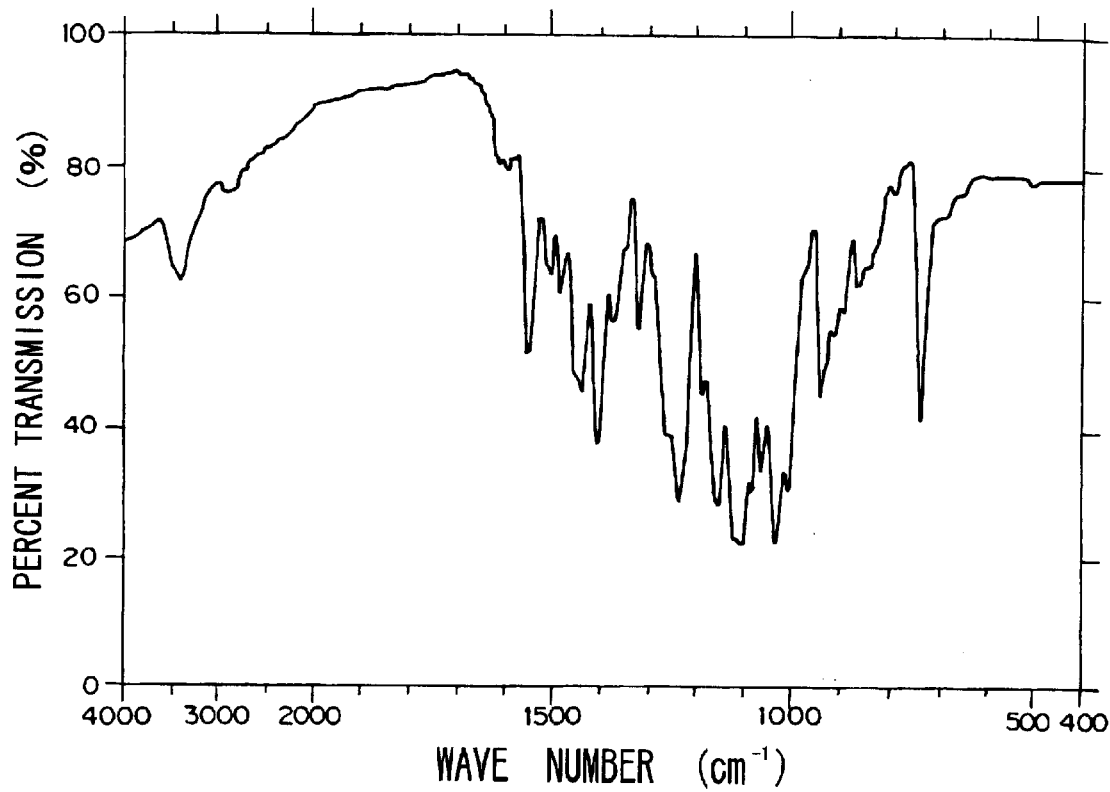
F I G . 8

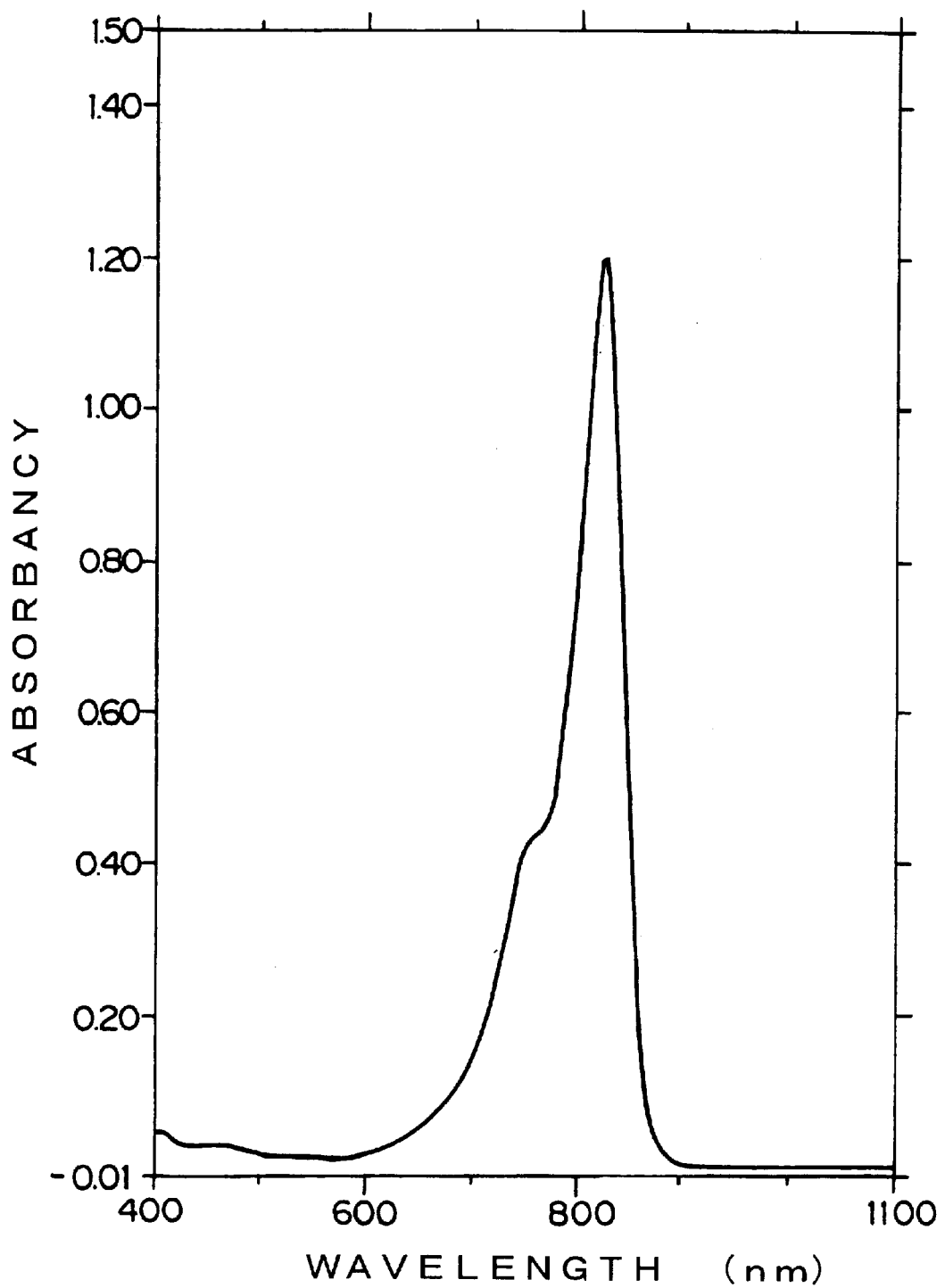
F I G. 1 1

POLYMETHINE COMPOUNDS, METHOD OF PRODUCING SAME, AND USE THEREOF

TECHNICAL FIELD

The present invention relates to a novel polymethine compound, a method of producing the same and a near infrared absorbing material comprising the same. The polymethine compound of the present invention absorbs in the near infrared region of 750~900 nm and can be used as a near infrared absorbing material in image recording utilizing laser beams, for example a near infrared absorbing material in plate making utilizing laser beams or in producing laser heat-sensitive recording media. It can further be utilized as a spectral sensitization dye in electrophotography or silver halide photography, or a dye for optical disks, for instance.

BACKGROUND OF THE INVENTION

With recent advances in laser technology, systems of image recording utilizing laser beams have been explored for implementing high-speed recording or high-density, high-image-quality recording. Thus, studies are in progress on image forming systems using laser heat-sensitive recording materials or laser thermal transfer recording materials, for instance, as recording systems in which a laser beam is converted to heat. Furthermore, the rapid spread of computers and progress in electronics, such as improvements in digital image processing technology gave impetus to an active endeavor to develop the so-called computer-to-plate technique (CTP plate making technique), which makes printing plates directly from digital data.

In the system of recording images through conversion of laser beams to heat (laser thermal recording system), a light absorbing material appropriate to the laser wavelength is used to convert the light absorbed to heat to thereby form images. However, unless the laser output is increased markedly, the heat energy required for image formation can hardly be obtained. Therefore, the advent of a light absorbing material with good light-to-heat conversion efficiency has been awaited. In laser thermal recording, semiconductor lasers are generally used which have light emission bands in the near infrared region of 750 nm to 900 nm. Near infrared absorbing materials matching such laser wavelengths generally absorb in the visible region as well and tend to cause objectional coloration of the background. Thus, a near infrared absorber less absorbing in the visible region of the spectrum is desired.

In the CTP plate making technology, known plate making methods are classifiable into the irradiating method using a laser beam, the method comprising writing by means of a thermal head, the method comprising applying a voltage locally by means of a pin electrode, the method comprising forming an ink-repelling or ink-receiving layer with an ink jet, and so forth. Among them, the method using a laser beam is superior in resolution and in the speed of plate making to other techniques, so that various image forming techniques for practicing said method have been investigated.

Further, recently, small-sized, high-output inexpensive semiconductor lasers having light emission bands in the near infrared region (750 nm to 900 nm) have become readily available and are coming to be utilized as exposure light sources in plate making.

There are two types of direct plate making utilizing laser beams, namely the photosensitive type and heat-sensitive type. As the photosensitive type plate material, there are known the electrophotographic system using an organic semiconductor (OPC), the silver salt system using a silver salt, and so on. These plate materials require a large-size and expensive equipment for the manufacture thereof and are relatively expensive as compared with the conventional presensitized (PS) plates. There is also the problem associated with the disposal of the used developer.

Heat-sensitive plate materials are disadvantageous in that they are low in sensitivity as compared with the photosensitive type plate materials. Nevertheless, they have been intensively investigated since they can be handled under ordinary interior conditions (in lighted rooms) and the equipment required is small in size and inexpensive.

All heat-sensitive plate materials require a light-to-heat conversion layer for converting light to heat. This light-to-heat conversion layer contains a light-to-heat conversion agent, for example a near infrared absorbing material. It is essential for such a light-to-heat conversion agent to absorb the laser beam used and, for attaining improved sensitivity, it is necessary that both the ability to absorb the laser beam used and the light-to-heat conversion efficiency thereof be sufficiently high.

The light-to-heat conversion agent includes pigment type and dye type agents. Carbon black is generally used as a pigment type agent. While various substances have been proposed as dye type agents, polymethine compounds are in widespread use. For carbon black, there is a wide assortment of lasers to choose from. However, carbon black is generally less efficient to absorb laser beams as compared with dye type substances, thus calling for its use in an increased amount. A high-level dispersion technique is also required.

In cases where a dye type substance is used, it is necessary that it be highly capable of absorbing the laser beam used and that it be well compatible with other components such as the image forming component and resin binder and well soluble in the solvent employed.

Polymethine compounds have a methine chain linked by conjugated double bonds within the molecule, absorb in a broad range of the spectrum from the visible to the near infrared region (340 to 1,400 nm) and have high extinction coefficients at their absorption maxima. For these and other reasons, polymethine compounds are used in various fields, for example as photosensitive dyes for silver salt photography, photosensitive dyes for electrophotography, dyes for laser recording, or dyes for laser light generation.

Although polymethine compounds are highly capable of absorbing laser beams, they have several problems to be solved: the compound matching the laser beam must be selected and most known compounds are deficient in light stability and poorly compatible with image forming substances and binder resins, among others.

A large number of polymethine compounds are already known and compounds having a ring structure interrupting the methine chain for enhanced durability have been developed. For example, Compound A is disclosed in JP Kokai S63-319191 (page 3, Compound 9) and Compound B in Journal of Organic Chemistry, 60, 2392, Table 1.

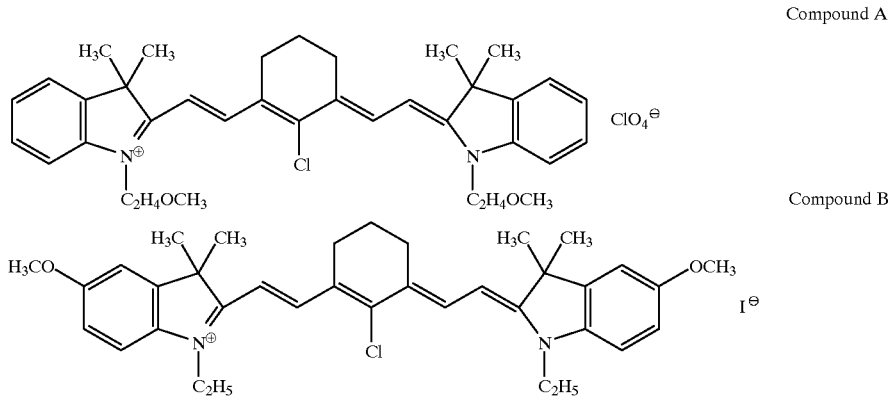

Compound A

Compound B

However, Compound A and Compound B both have maximum absorption wavelengths within the range of 785~815 and are not sensitive enough to small-sized high-output lasers having light emissions in the range of 820~840 nm. Moreover, both Compound A and Compound B are deficient in solvent solubility and compatibility with resins, so that the kind of binder resin that can be used is limited.

OBJECT AND SUMMARY OF THE INVENTION

The present invention has for its object to provide a polymethine compound which absorbs little in the visible region of the spectrum, is highly sensitive to semiconductor lasers having emission bands in the near infrared region (750~900 nm), especially between 820~840 nm and, as such, is useful as a near infrared absorbing material or suited for use in the light-to-heat conversion layer of a laser thermal recording medium or a CTP plate.

After a multi-pronged investigation, the inventors of the present invention discovered a novel polymethine compound, which absorbs little in the visible region of the spectrum, has good sensitivity to semiconductor lasers having emission bands in the near infrared region (750~900 nm) and a high light-to-heat conversion efficiency. Further, this compound can be used as a near infrared absorbing material, which can be easily processed for various applications.

The first invention in the instant application is concerned with a polymethine compound of the following general formula (I).

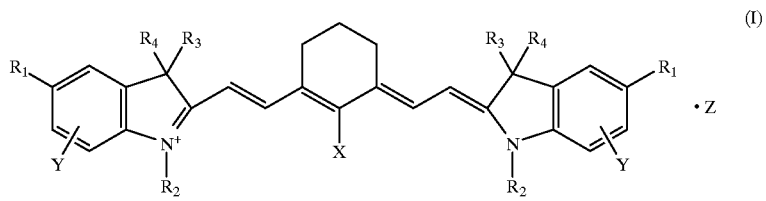

(I)

wherein $R_1$ represents an alkoxy group which may be substituted; $R_2$ represents an alkyl group which may be substituted; $R_3$ and $R_4$ each represents a lower alkyl group or $R_3$ and $R_4$ taken together represent a ring; X represents a hydrogen atom, a halogen atom or a substituted amino group; Y represents an alkoxy group which may be substituted or an alkyl group which may be substituted; Z represents a charge neutralizing ion.

The second invention is concerned with a crystal modification, crystalline methanol adduct or amorphous form of a polymethine compound of the following formula.

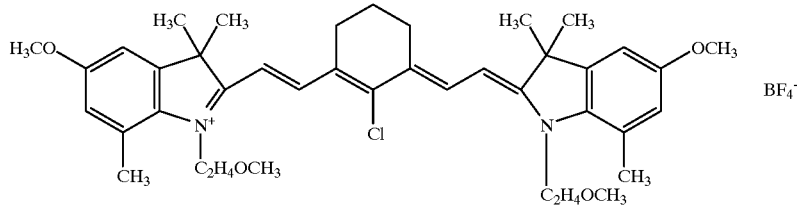

The third invention is concerned with a process for producing a polymethylene compound of the above general formula (I) which comprises condensing an indolenium compound of the following general formula (II) with either a diformyl compound of the following general formula (III) or a dianil compound of the following general formula (IV) using a dehydrating organic acid in the presence of a fatty acid salt.

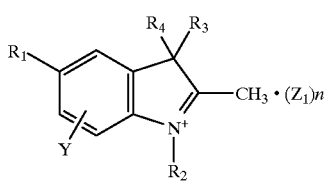

(II)

wherein $R_1$ represents an alkoxy group which may be substituted; $R_2$ represents an alkyl group which may be substituted; $R_3$ and $R_4$ each represents a lower alkyl group or $R_3$ and $R_4$ taken together represent a ring; Y represents an alkoxy group which may be substituted or an alkyl group which may be substituted; $Z_1$ represents a charge neutralizing ion; n represents a number of 0 or 1.

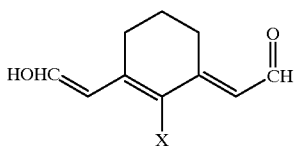

(III)

wherein X represents a hydrogen atom, a halogen atom or a substituted amino group.

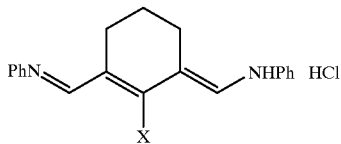

(IV)

wherein X represents a hydrogen atom, a halogen atom or a substituted amino group.

The fourth invention is concerned with a process for producing a high-melting crystalline compound which comprises recrystallizing said polymethine compound of the first invention from a ketonic or an alcoholic solvent.

The fifth invention is concerned with a process for producing a low-melting crystalline compound which comprises treating a crystalline solvate or amorphous form of said polymethine compound of the first invention with a herein-defined solvent.

The sixth invention is concerned with a near infrared absorbing material comprising said polymethine compound of the first invention.

The seventh invention is concerned with an original plate for direct printing plate (CTP printing plate) containing said polymethine compound of the first invention in its light-to-heat conversion layer as constructed on a support.

The eighth invention is concerned with a method of manufacturing a printing plate which comprises irradiating the original plate for direct printing plate of the seventh invention using a semiconductor laser having a light emission band of 750~900 nm as a light source.

BRIEF DESCRIPTION OF THE DRAWINGS

FIG. 8 is an IR absorption spectrum of the polymethine compound according to Example 8.

FIG. 11 is VIS-NIR absorption spectrum of the polymethine compound according to Example 7 in diacetone alcohol.

DETAILED DESCRIPTION OF THE INVENTION

Figure 1:
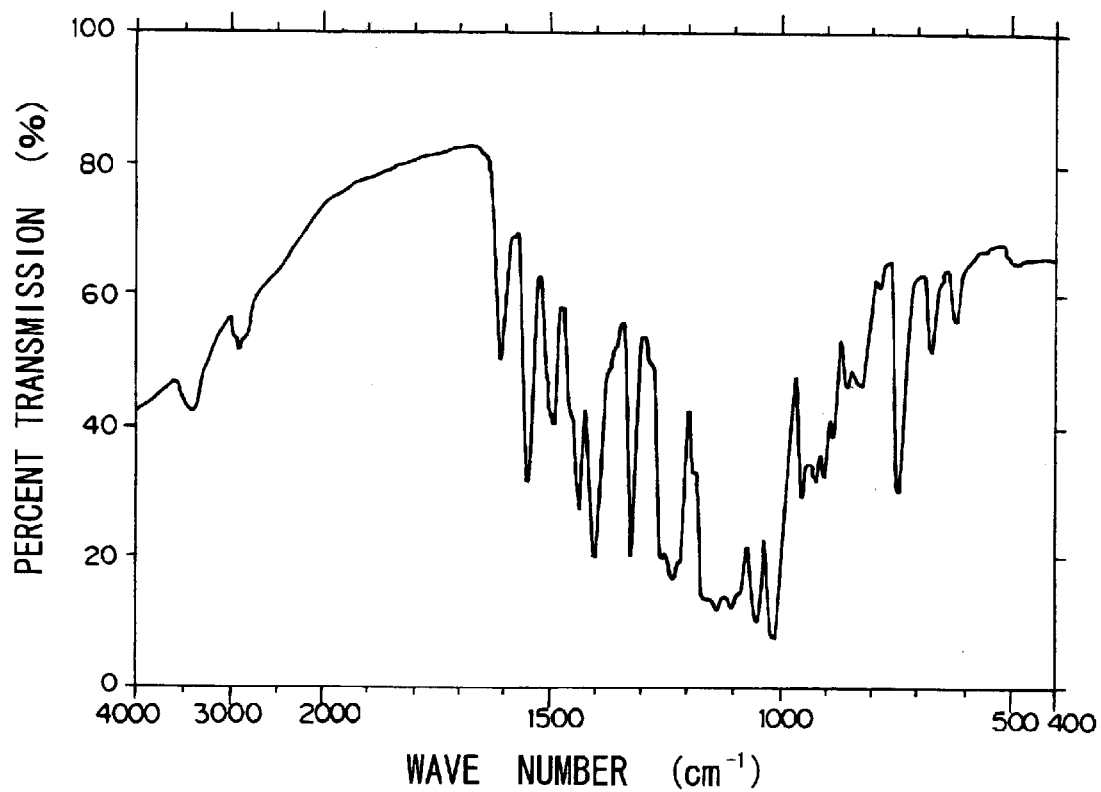
FIG. 1 is an IR absorption spectrum of the polymethine compound according to Example 1.

In the following, the present invention is described in detail.

[Polymethine compound]

First, the polymethine compound of the following general formula (I) according to the first invention and the crystal modification, crystalline methanol adduct or amorphous form of 2-(2-{2-chloro-3-[(1,3-dihydro-3,3,7-trimethyl-5-methoxy-1-methoxyethyl-2H-indol-2-ylidene)ethylidene]-1-cyclohexen-1-yl}ethenyl)-3,3,7-trimethyl-5-methoxy-1-methoxyethylindolium=tetrafluoroborate [Compound species (55)] according to the second invention are now described in detail.

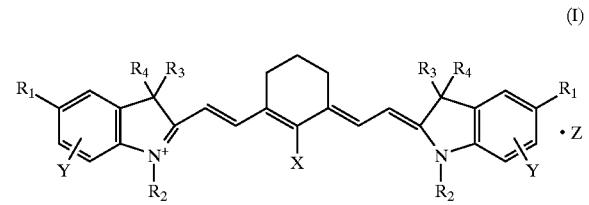

(I)

wherein $R_1$ represents an alkoxy group which may be substituted; $R_2$ represents an alkyl group which may be substituted; $R_3$ and $R_4$ each represents a lower alkyl group or $R_3$ and $R_4$ taken together represent a ring; X represents a hydrogen atom, a halogen atom or a substituted amino group; Y represents an alkoxy group which may be substituted or an alkyl group which may be substituted; Z represents a charge neutralizing ion.

The alkoxy group for $R_1$, when it is an unsubstituted alkoxy group, is preferably a group of 1~8 carbon atoms, particularly 1~4 carbon atoms.

The alkoxy group $R_1$, when substituted, may have such substituents as alkyloxy, alkylthio, hydroxy and halogen, although alkyloxy groups are preferred. The alkoxy group $R_1$ having an alkyloxy group is preferably a group containing a total of 2~8 carbon atoms, more preferably a total of 2~4 carbon atoms.

To mention specific examples, the alkoxy group $R_1$ includes methoxy, ethoxy, n-propoxy, iso-propoxy, n-butoxy, iso-butoxy, sec-butoxy, n-pentoxy, iso-pentoxy, n-octyloxy, 2-ethylhexyloxy, methoxymethoxy, 2-methoxyethoxy and 2-ethoxyethoxy.

When $R_2$ represents an unsubstituted alkyl group, this group is preferably a straight-chain or branched-chain alkyl group of 1 to 18 carbon atoms, more preferably a straight-chain or branched-chain alkyl group of 1 to 8 carbon atoms. Examples are methyl, ethyl, n-propyl, isopropyl, n-butyl, isobutyl, sec-butyl, n-pentyl, isopentyl, neopentyl, n-hexyl, isohexyl, sec-hexyl, 2-ethylbutyl, n-heptyl, isoheptyl, sec-heptyl, n-octyl, 2-ethylhexyl, n-decyl, n-dodecyl, n-pentadecyl and n-octadecyl, among others.

When $R_2$ represents a substituted alkyl group, this group may be an alkoxyalkyl group, a sulfoalkyl group or a carboxyalkyl group, for instance. The alkoxyalkyl group mentioned just above preferably contains 2 to 8 carbon atoms. As examples, there may be mentioned 2-methoxyethyl, 3-methoxypropyl, 4-methoxybutyl, 2-ethoxyethyl, 3-ethoxypropyl, 4-ethoxybutyl, 2-n-propoxyethyl, 2-isopropoxyethyl, 3-n-propoxypropyl, 4-n-propoxybutyl, 2-methoxy-2-ethoxyethyl and 2-ethoxy-2-ethoxyethyl.

The sulfoalkyl group mentioned above for $R_2$ is preferably a straight-chain or branched-chain sulfoalkyl group of 1 to 18 carbon atoms, more preferably a straight-chain or branched-chain sulfoalkyl group of 1 to 8 carbon atoms. Preferably, at least one of these sulfoalkyl groups represented by $R_2$ be in the form of a salt with an alkali metal ion or an alkylammonium ion. As examples of such sulfoalkyl group, there may be mentioned 2-sulfoethyl, 3-sulfopropyl, 3-sulfobutyl, 4-sulfobutyl, 4-sulfo-3-methylbutyl, 2-(3-sulfopropoxy)ethyl, 2-hydroxy-3-sulfopropyl, 3-sulfo-2-(2-ethoxy)ethoxypropoxy, 5-sulfopentyl, 6-sulfohexyl, 8-sulfooctyl and 6-sulfo-2-ethylhexyl, and these may each be in the form of a salt with an alkali metal ion or an alkylammonium ion.

The carboxyalkyl group mentioned above for $R_2$ is preferably a straight-chain or branched-chain carboxyalkyl group of 2 to 18 carbon atoms, more preferably a straight-chain or branched-chain carboxyalkyl group of 2 to 9 carbon atoms. Preferably, at least one of these carboxyalkyl groups represented by $R_2$ is in the form of a salt with an alkali metal ion or an alkylammonium ion. As examples of such carboxyalkyl group, there may be mentioned 2-carboxyethyl, 3-carboxypropyl, 3-carboxybutyl, 4-carboxybutyl, 4-carboxy-3-methylbutyl, 2-(3-carboxypropoxy)ethyl, 2-hydroxy-3-carboxypropyl, 3-carboxy-2-(2-ethoxy) ethoxypropoxy, 5-carboxypentyl, 6-carboxyhexyl, 8-carboxyoctyl and 6-carboxy-2-ethylhexyl, and these may each be in the form of a salt with an alkali metal ion or an alkylammonium ion.

The lower alkyl group represented by each of $R_3$ and $R_4$ may, for example, be methyl, ethyl, n-propyl, isopropyl, n-butyl, isobutyl or sec-butyl.

The ring structure formed by $R_3$ and $R_4$ taken together may, for example, be a cyclopropane, cyclobutane, cyclopentane, cyclohexane or cycloheptane ring. Among them, the cyclobutane, cyclopentane and cyclohexane rings are preferred.

X represents hydrogen, halogen, (e.g. F, Cl, Br, I), or a substituted amino group, such as ethylamino, phenylamino, diphenylamino or morpholino, preferably Cl, Br or diphenylamino.

When Y is an unsubstituted alkoxy group, it is preferably an alkoxy group of 1~8 carbon atoms, more preferably 1~4 carbon atoms.

When Y is a substituted alkoxy group, the substituent includes alkyloxy, alkylthio, hydroxy and halogen, preferably alkyloxy. When Y is an alkoxy group having an alkyloxy group as a substituent, it is preferably an alkoxy group containing a total of 2~8 carbon atoms, more preferably one containing 2~4 carbon atoms.

The alkoxy group Y, as such, includes methoxy, ethoxy, n-propoxy, iso-propoxy, n-butoxy, iso-butoxy, sec-butoxy, n-pentoxy, iso-pentoxy, n-octyloxy, 2-ethylhexyloxy, 2-methoxyethoxy and 2-ethoxyethoxy, among others.

When Y is an unsubstituted alkyl group, it is preferably a straight-chain or branched-chain alkyl group of 1~8 carbon atoms, more preferably one of 1~4 carbon atoms. As examples, there may be mentioned methyl, ethyl, n-propyl, isopropyl, n-butyl, isobutyl, sec-butyl, n-pentyl, isopentyl, neopentyl, n-hexyl, isohexyl, sec-hexyl, 2-ethylbutyl, n-heptyl, isoheptyl, sec-heptyl, n-octyl and 2-ethylhexyl.

When Y is a substituted alkyl group, the substituent includes alkyloxy, alkylthio, hydroxy, halogen, etc. but is preferably alkyloxy. When Y is an alkyl group having an alkyloxy group as a substituent, it is preferably one containing a total of 2~4 carbon atoms. As specific examples, there may be mentioned 2-methoxyethyl, 3-methoxypropyl, 4-methoxybutyl, 2-ethoxyethyl, 3-ethoxypropyl, 4-ethoxybutyl, 2-n-propoxyethyl, 2-iso-propoxyethyl, 3-n-propoxypropyl, 4-n-propoxybutyl, 2-methoxy-2-ethoxyethyl, and 2-ethoxy-2-ethoxyethyl.

Z represents a charge neutralizing ion and may, for example, be $F^-$, $Cl^-$, $Br^-$, $I^-$, $BrO_4^-$, $ClO_4^-$, p-toluenesulfonate, $CH_3SO_3^-$, $BF_4^-$, $CH_3CO_2^-$, $CF_3CO_2^-$, $PF_6^-$, $SbF_6^-$, $Na^+$, $K^+$ or triethylammonium ion. Particularly preferred among these are $Cl^-$, $Br^-$, $I^-$, $ClO_4^-$, p-toluenesulfonate, $CH_3SO_3^-$, $BF_4^-$, $CF_3CO_2^-$, $PF_6^-$, $SbF_6^-$, $Na^+$, $K^+$, and triethylammonium ion.

$Z_1$ represents a charge neutralizing ion and may, for example, be $F^-$, $Cl^-$, $Br^-$, $I^-$, $BrO_4^-$, $ClO_4^-$, p-toluenesulfonate, $CH_3SO_3^-$, $BF_4^-$, $CH_3CO_2^-$, $CF_3CO_2^-$, $PF_6^-$ or $SbF_6^-$. Particularly preferred among these are $Cl^-$, $Br^-$, $I^-$, $CO_4^-$, p-toluenesulfonate, $CH_3SO_3^-$, $BF_4^-$, $CF_3CO_2^-$, $PF_6^-$ and $SbF_6^-$.

The following is a partial listing of the preferred examples of the polymethine compound of general formula (I).

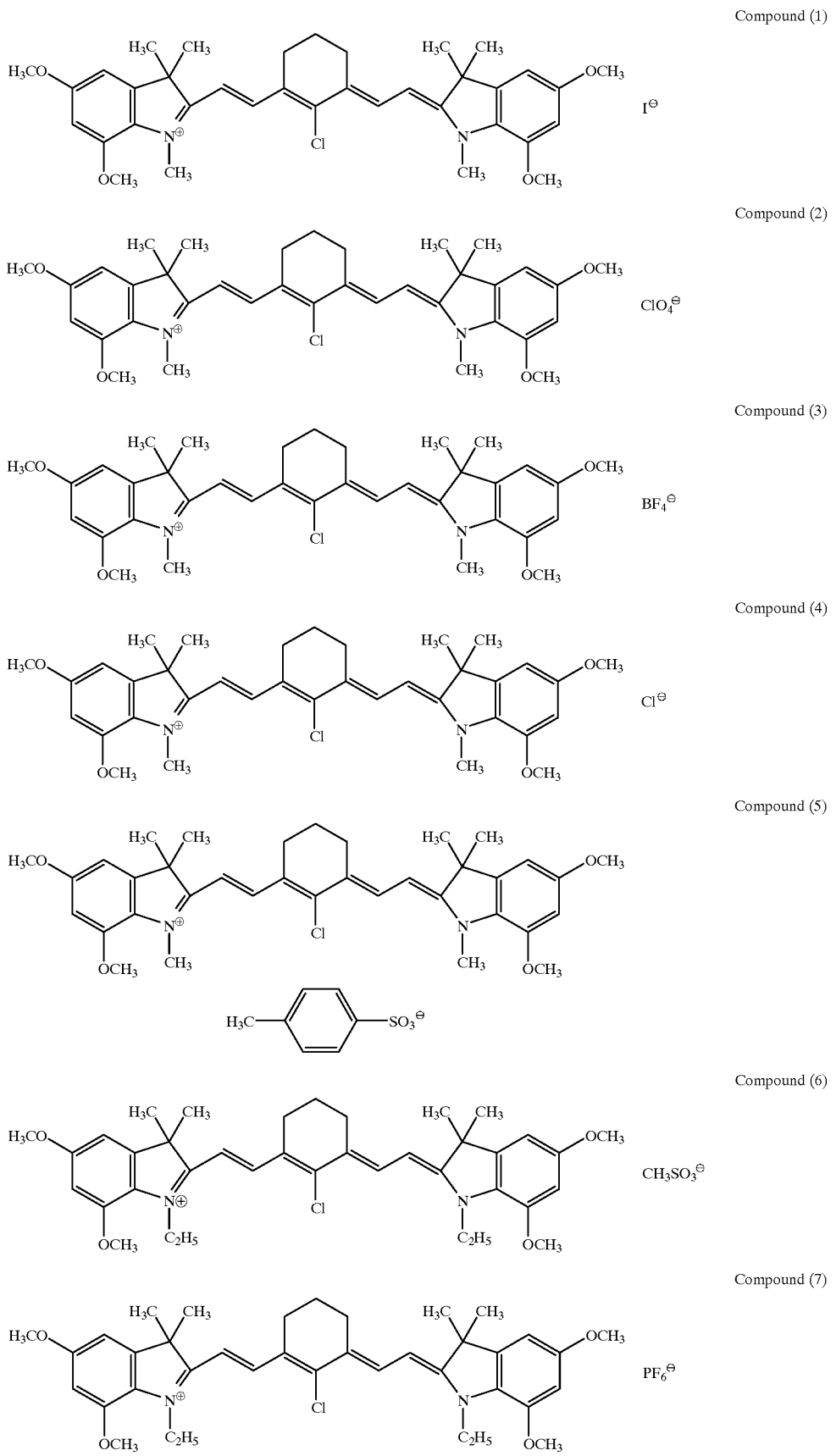

-continued
Compound (8)
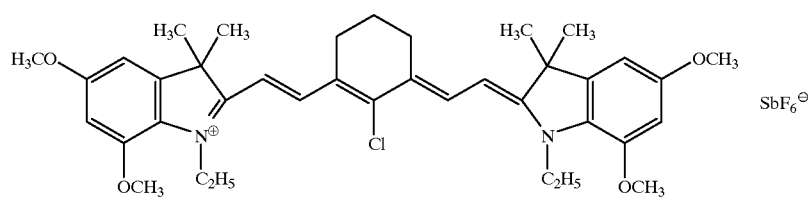
Compound (9)
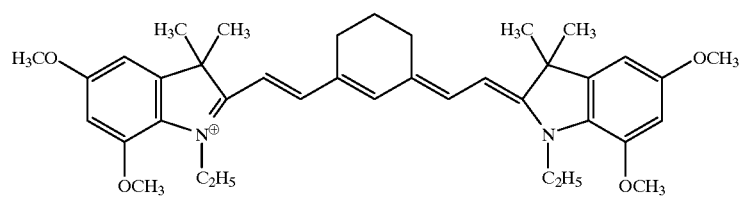
Compound (10)
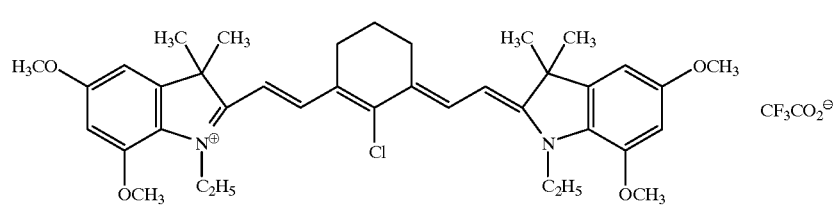
Compound (11)
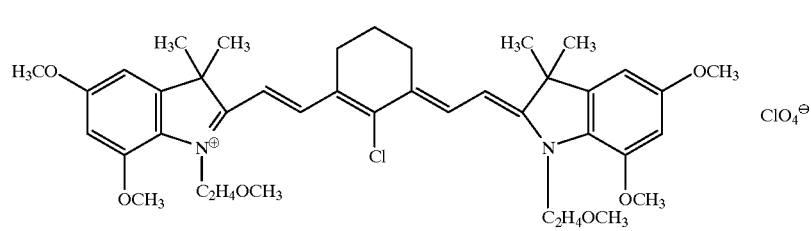
Compound (12)
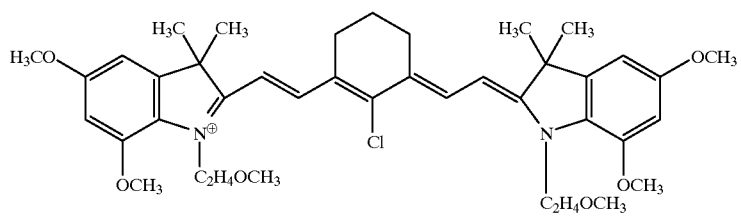
Compound (13)
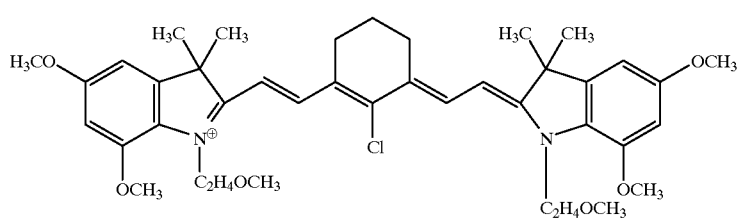
Compound (14)
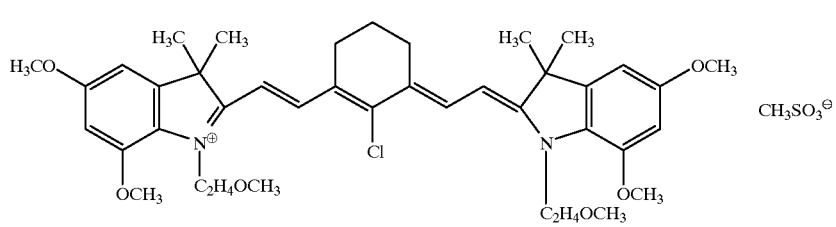

-continued
Compound (15)
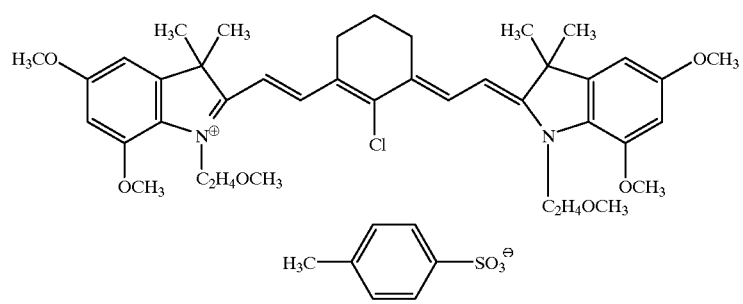
Compound (16)
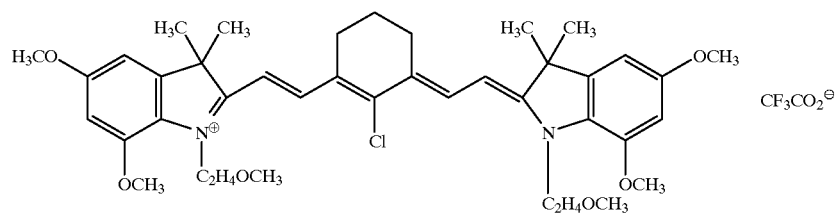
Compound (17)
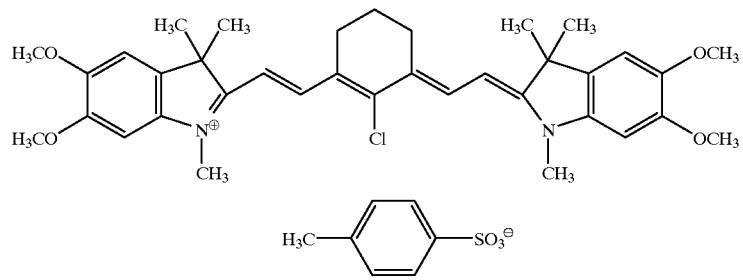
Compound (18)
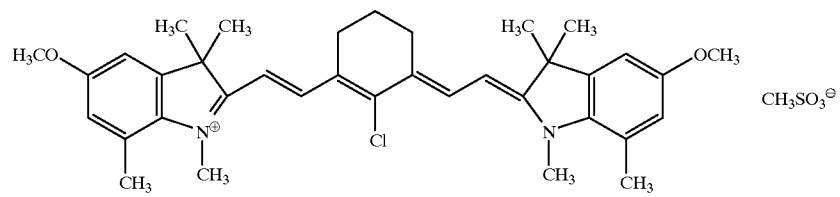
Compound (19)
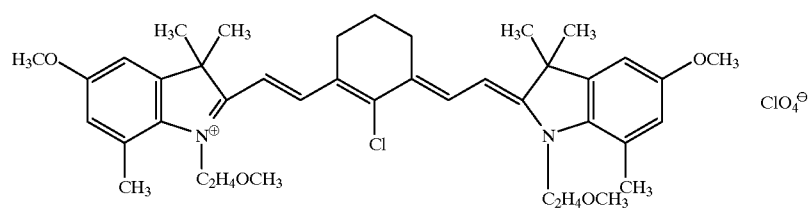
Compound (20)
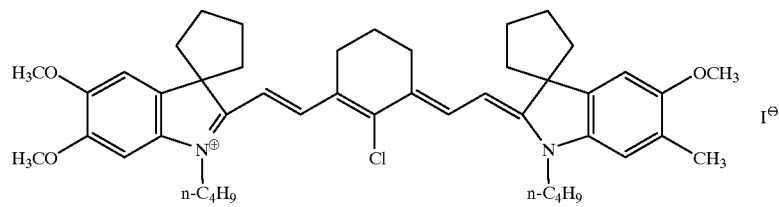

-continued
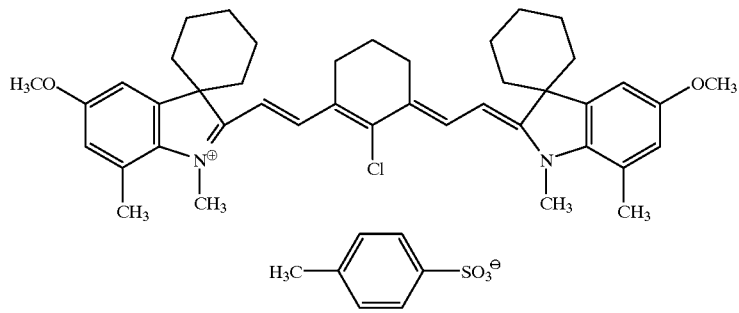
Compound (21)
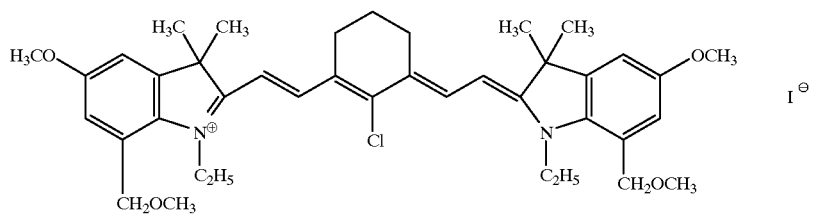
Compound (22)
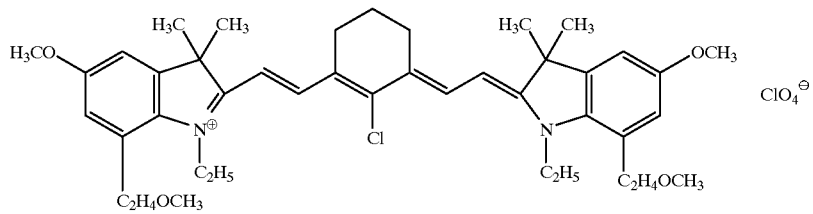
Compound (23)
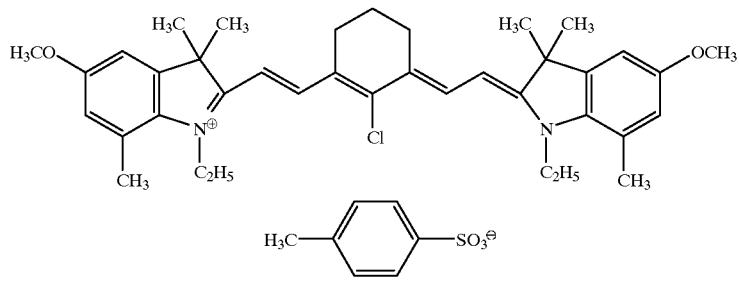
Compound (24)
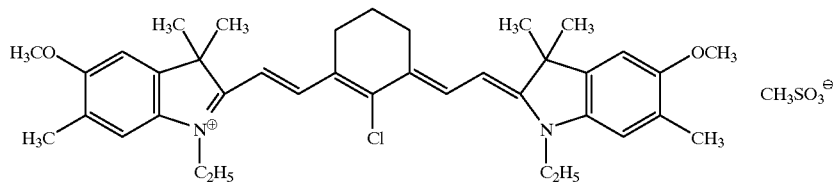
Compound (25)
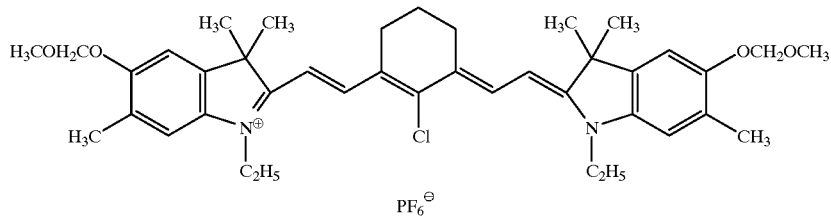
Compound (26)

-continued
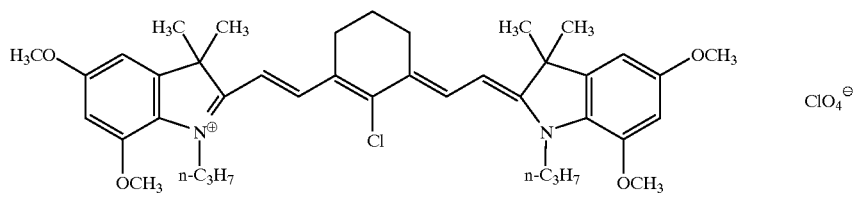
Compound (27)
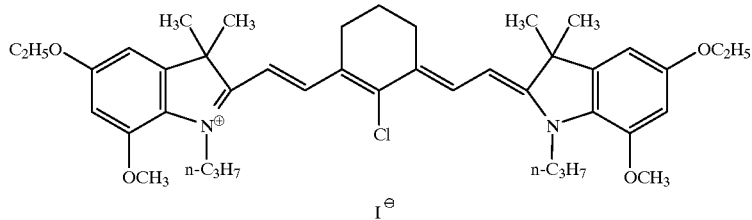
Compound (28)
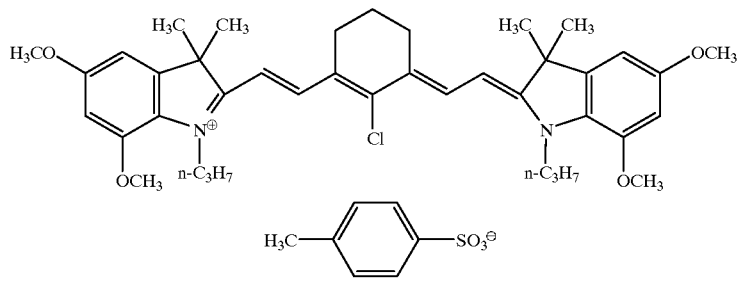
Compound (29)
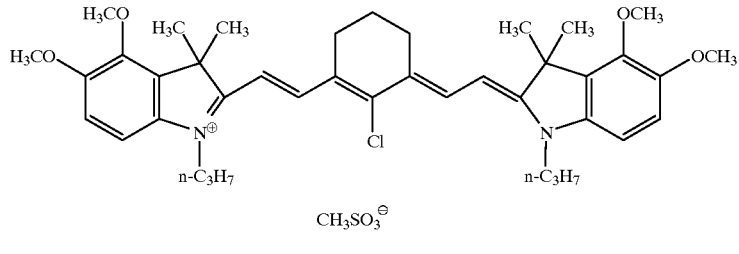
Compound (30)
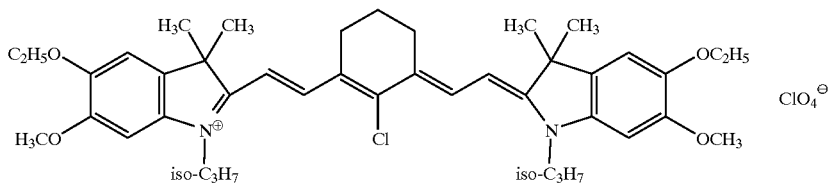
Compound (31)
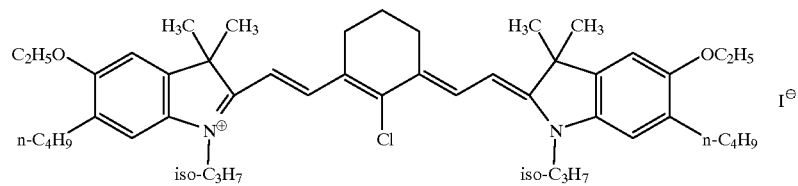
Compound (32)

-continued
Compound (33)
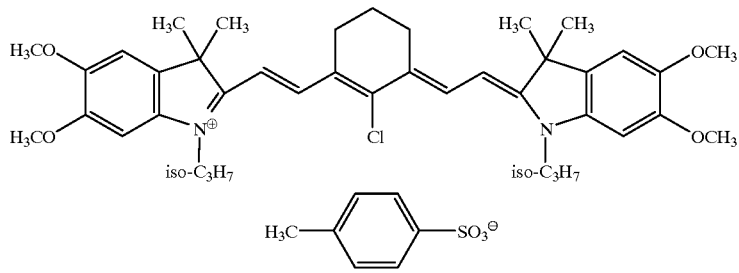
Compound (34)
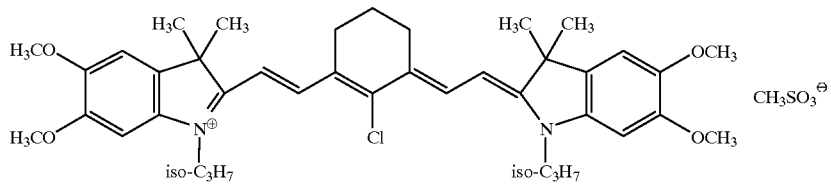
Compound (35)
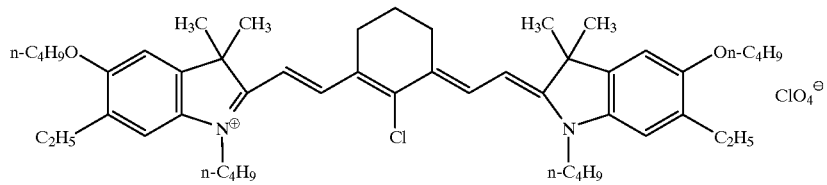
Compound (36)
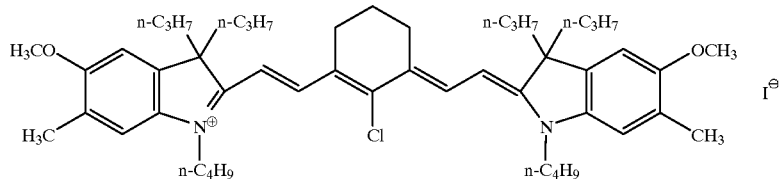
Compound (37)
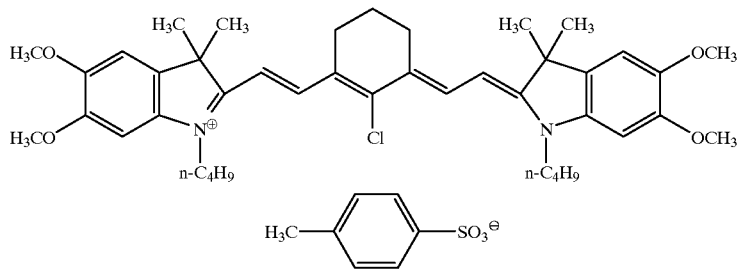
Compound (38)
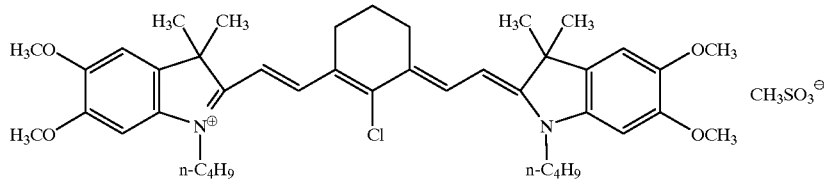
Compound (39)
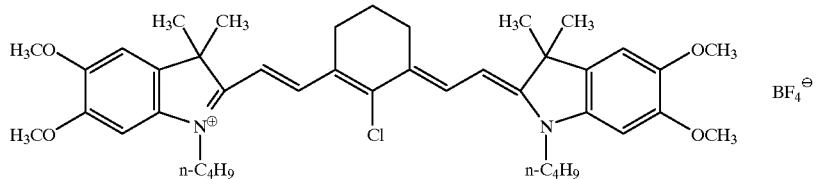

-continued
Compound (40)
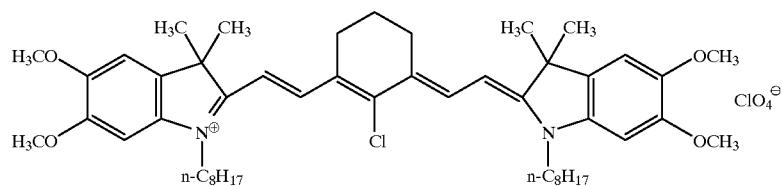
Compound (41)
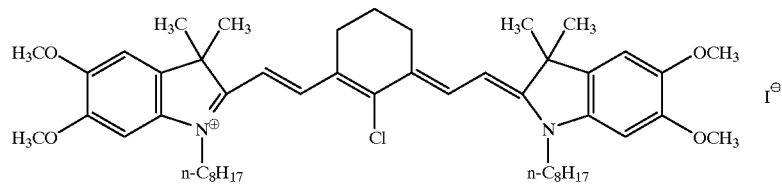
Compound (42)
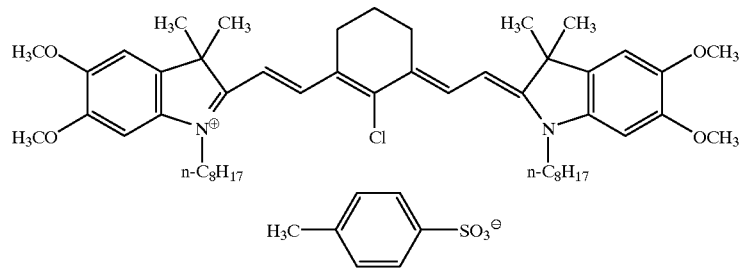
Compound (43)
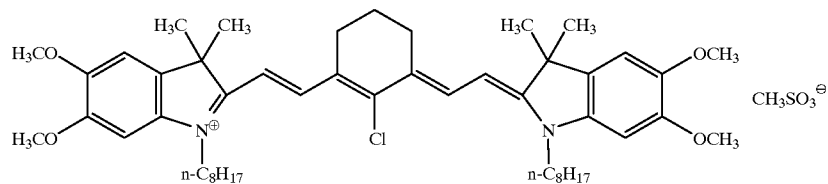
Compound (44)
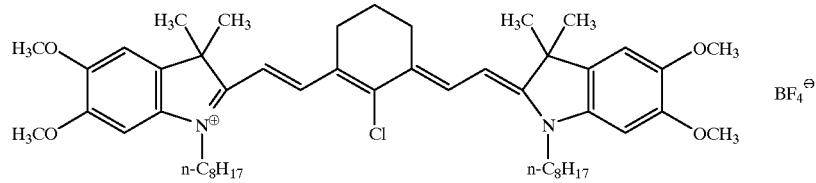
Compound (45)
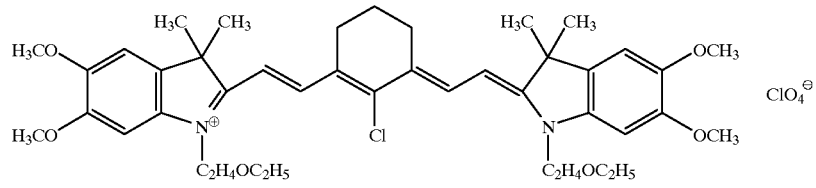
Compound (46)
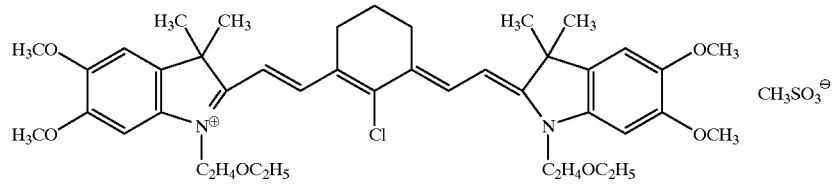

Compound (47)
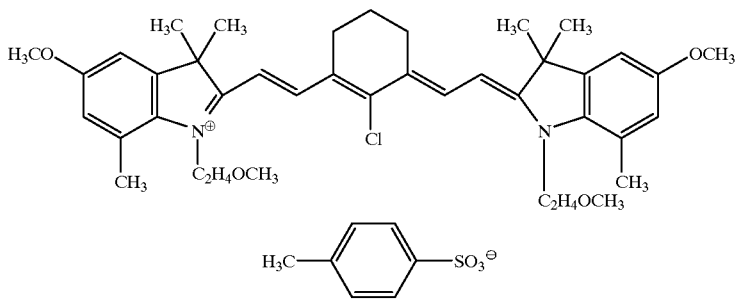
Compound (48)
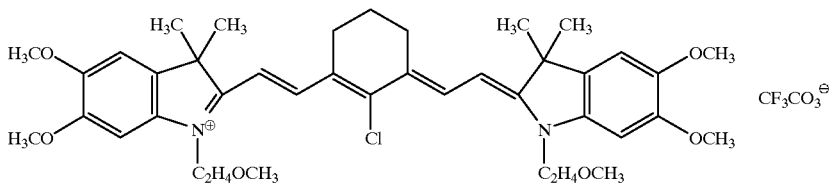
Compound (49)
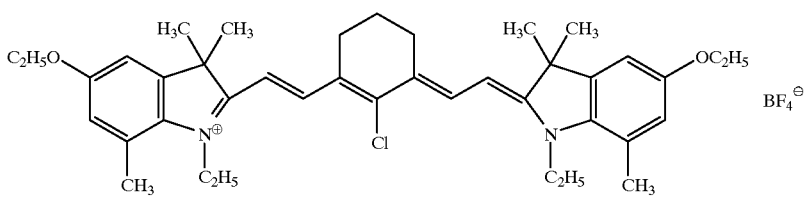
Compound (50)
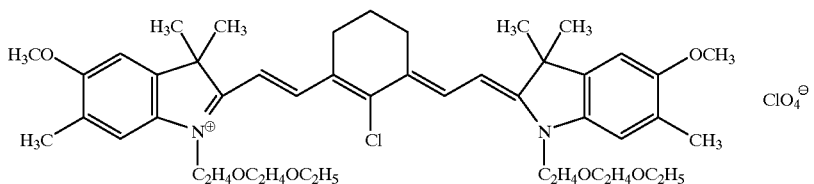
Compound (51)
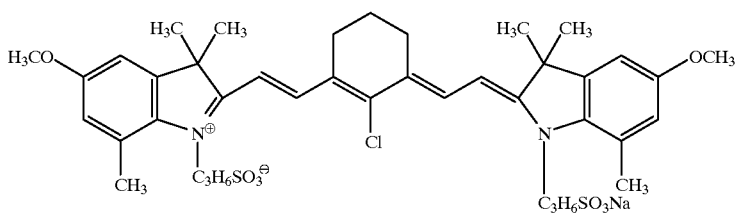
Compound (52)
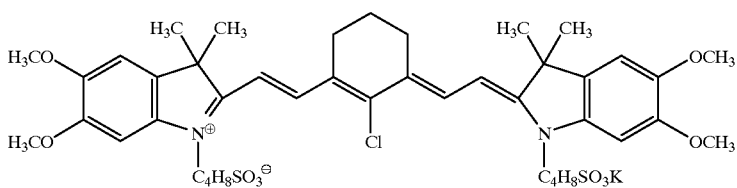
Compound (53)
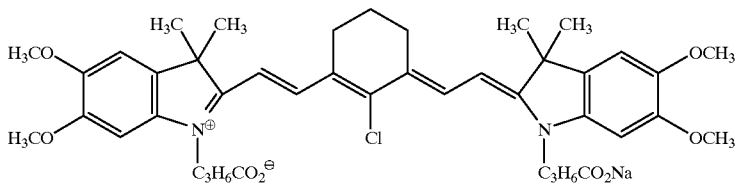

-continued
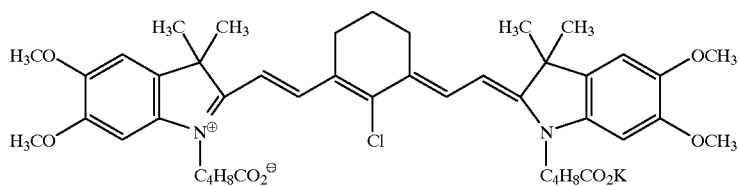
Compound (54)
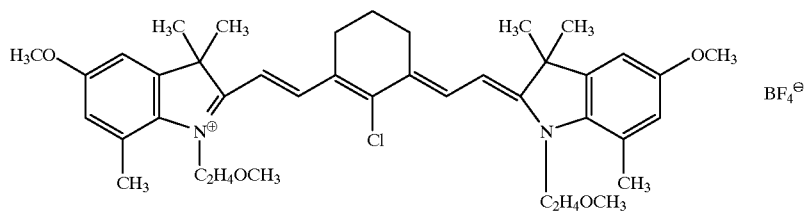
Compound (55)
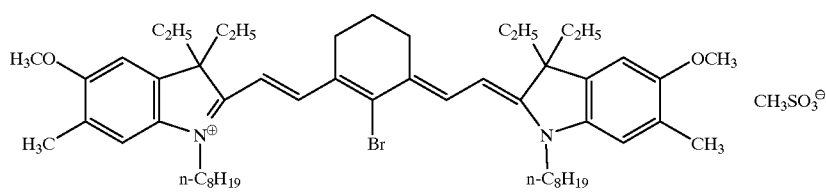
Compound (56)
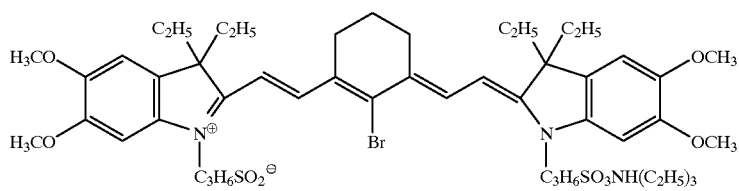
Compound (57)
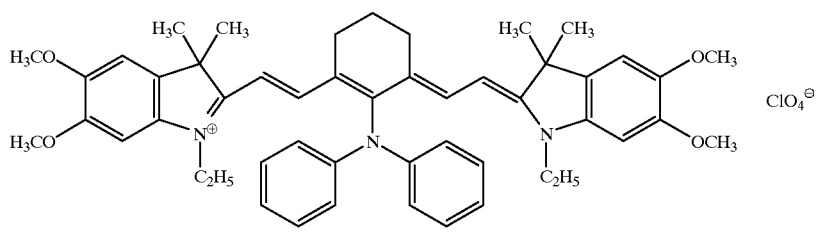
Compound (58)
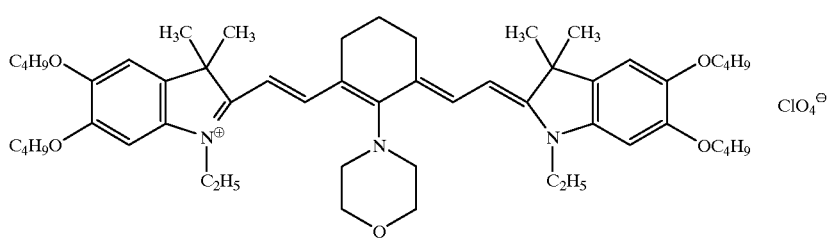
Compound (59)
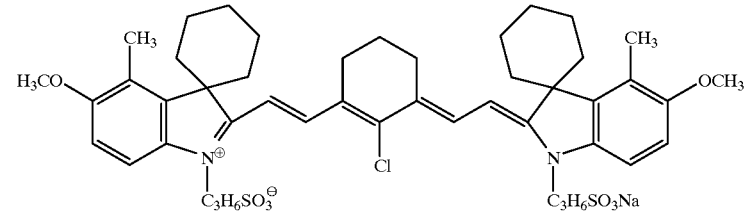
Compound (60)

Compound (61)
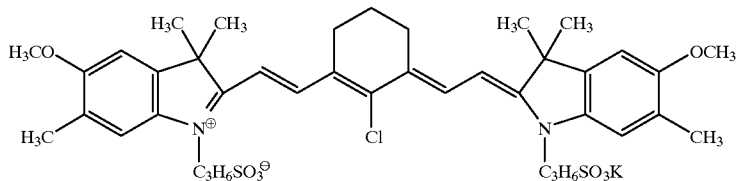
Compound (62)
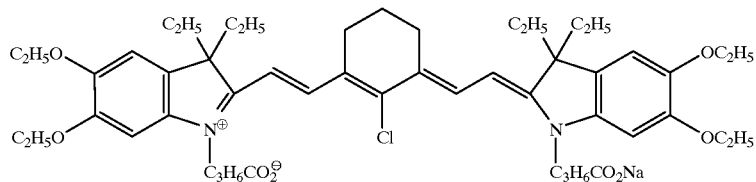
Compound (63)
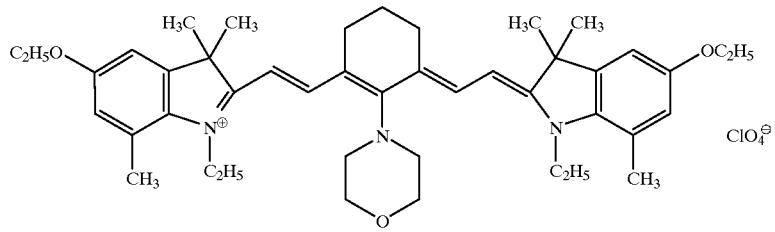
Compound (64)
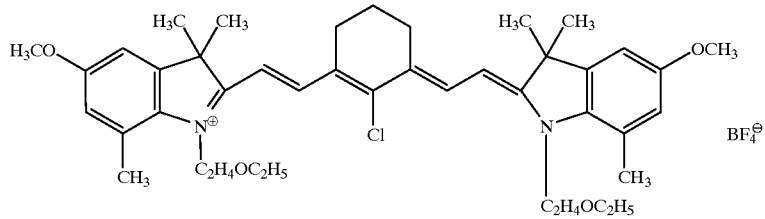
Compound (65)
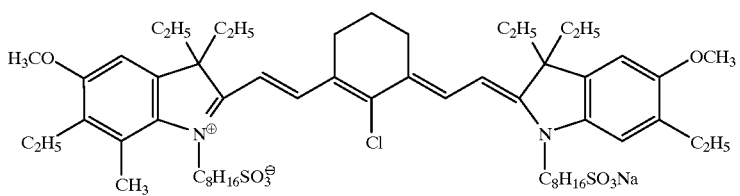
Among the compounds (1) through (65) mentioned above as specific examples, the compounds represented by the following general formula (V) may alternatively be represented by the general formula (VI) given below.
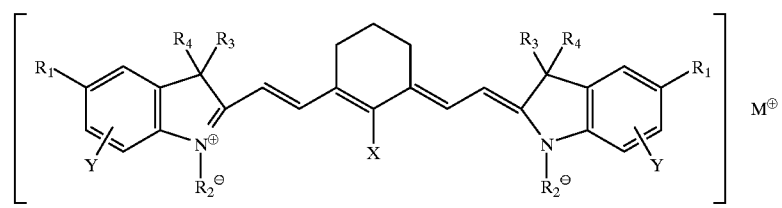
(V)

(VI)

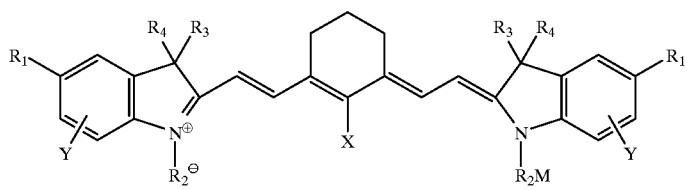

wherein $R_1$~$R_4$, X and Y are respectively as defined above;
M represents Na, K or triethylammonium.

For example, Compound (51) may optionally be written as follows.

Compound (51)

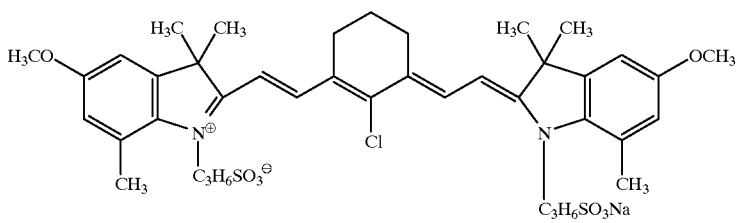

Among specific polymethine compounds of general formula (I) according to the invention, some may occur as crystal modifications, crystalline solvates and amorphous compounds. For example, Compound (55) may exist as the a-crystal (low-melting compound) which, in the powder X-ray diffractometry using the Cu—Kα rays, shows characteristic peaks at the diffraction angles (2θ±0.2°) of 11.6°, 14.6°, 15.6°, 19.6° and 22.9°, the β-crystal (high-melting compound) which shows a characteristically strong peak at the diffraction angles (2θ±0.2°) of 8.4°, the crystalline methanol adduct which shows characteristic peaks at the diffraction angles (2θ±0.2°) of 13.3°, 17.4°, 19.8°, 21.8° and 26.9°, and the amorphous compound showing no characteristic diffraction (2θ±0.2°) peak.

[Method for production of the polymethine compound and its crystal modification]

The polymethine compound of the present invention can be typically produced by subjecting an indolenium compound represented by the general formula (II) and a diformyl compound represented by the general formula (III) or a dianil compound represented by the general formula (IV) to condensation reaction in the presence of a fatty acid salt in a dehydrating organic acid.

(II)

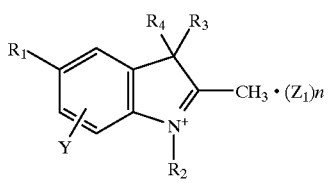

(In the above formula, $R_1$~$R_4$, Y, $Z_1$ and n are respectively as defined above.)

(III)

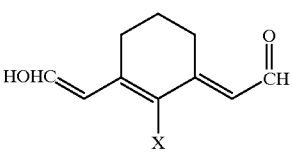

(In the above formula, X is as defined above.)

(IV)

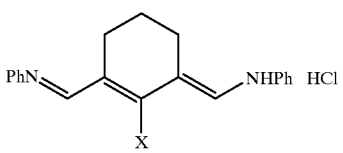

(In the above formula, X is as defined above.)

In the above condensation reaction, the fatty acid salt is, for example, sodium acetate, potassium acetate, calcium acetate, sodium propionate, potassium propionate or the like.

Such fatty acid salt is used generally in an amount of about 0.1 to 5 moles, preferably about 0.5 to 2 moles, per mole of the compound of general formula (III).

As the dehydrating organic acid, there may be mentioned acetic anhydride, propionic anhydride, butyric anhydride, γ-butyrolactone and the like.

Such dehydrating organic acid is used generally in an amount of about 10 to 100 moles, preferably about 20 to 50 moles, per mole of the compound of general formula (II).

As to the ratio of the compound of general formula (II) to the compound of general formula (III) or (IV) the latter is used generally in an amount of about 0.2 to 1.5 moles, preferably about 0.4 to 0.7 moles, per mole of the former.

The above reaction can proceed generally at about 10 to 150° C., preferably at room temperature to 120° C., and will go to completion generally in several minutes to about 3 hours.

After the reaction, the desired product can be readily isolated from the reaction mixture, for example, by pouring a poor solvent, such as water, methanol, ethanol, n-propanol, isopropanol or n-butanol, into said mixture or discharging said mixture into a poor solvent such as water, methanol, ethanol, n-propanol, isopropyl alcohol or n-butanol. The product can be readily purified in the conventional manner, for example by recrystallization, columnwise separation and/or other appropriate means.

Some species of the polymethine compound of general formula (I) according to the invention may exist as crystal modifications, crystalline solvates or amorphous forms and, depending on the method of isolation prior to purification and/or the method of purification, may each be available as a crystalline modification, crystalline solvate or an amorphous form or a mixture thereof.

Among such forms of the polymethine compound of the invention, the low-melting compound can be produced by treating the crystalline solvate or amorphous compound with a solvent, such as a ketone, an alcohol, or a mixture thereof with an ester and/or ether, for example by the contact method. This treatment is preferably carried out under conditions avoiding recrystallization, for example by dispersing the compound in a solvent the amount and temperature of which are so controlled that the solid polymethine compound is not completely dissolved. The contact treatment includes not only dispersing the polymethine compound in such a solvent or merely contacting the compound with the solvent.

The high-melting compound is a thermally stable crystalline compound and can be produced by a recrystallization method using a solvent in which the low-melting compound, crystalline solvate or amorphous compound or a mixture of the low-melting compound, high-melting compound, crystalline solvate and amorphous compound is thoroughly soluble, such as a ketone, an alcohol or a ketone-alcohol mixture. This recrystallization is preferably carried out by dissolving the polymethine compound thoroughly in the solvent and allowing the system to ripen gradually or adding seed crystals.

The ketone which can be used for such contact treatment or recrystallization includes a variety of carbonyl-containing solvents such as acetone, methyl ethyl ketone, methyl propyl ketone, methyl butyl ketone, methyl isopropyl ketone, methyl amyl ketone, diethyl ketone, ethyl butyl ketone, dipropyl ketone, diusopropyl ketone, diacetone alcohol, cyclohexanone, etc. The alcohol includes but is not limited to methanol, ethanol, n-propanol, isopropanol, n-butanol, isobutanol, sec-butanol, tert-butanol, n-amyl alcohol methylamyl alcohol, 2-ethylhexanol, n-octanol, cyclohexanol and 2-ethylcyclohexanol. The ester which can be used for the contact treatment includes methyl acetate, ethyl acetate, n-propyl acetate, isopropyl acetate, n-butyl acetate, isoamyl acetate, n-butyl butyrate, etc., and the ether includes diethyl ether, isopropyl ether, n-butyl ether and diglyme, among others.

The amount of the solvent to be used in the contact treatment for production of the low-melting compound is dependent on the solubility of the polymethine compound therein and may be 2~70 times by weight, preferably 3~50 times by weight, within the range not causing complete dissolution of the polymethine compound. If the amount of the solvent exceeds the above range, the product yield will be reduced to sacrifice the efficiency of production. The treating temperature varies with the kind of solvent but is generally about −10~70° C., preferably 0~50° C. To the solvent for the dispersion treatment, poor solvents such as esters and/or ethers can be added.

The amount of the recrystallization solvent for production of the high-melting compound is also dependent on the solubility of the polymethine compound therein, and may be 3~100 times by weight, preferably 5~70 times by weight, based on the polymethine compound within the range in which the polymethine compound is completely soluble. If the amount of the solvent is too small, the crystalline solvate tends to form under certain conditions. If the amount of the solvent is too large, the product yield will be reduced to sacrifice the efficiency of production. The recrystallization temperature is dependent on the solvent used but is generally about 20~150° C., preferably 30~120° C. As the recrystallization solvent, a ketone-alcohol mixture can be used.

Among species of the compound of general formula (I) according to the invention, the compound of the following formula, for instance, may assume a plurality of distinct forms varying in powder X-ray diffraction pattern, namely the low-melting compound (m.p. 195~197° C., α-crystal), high-melting compound (m.p. 204~206° C., β-crystal), crystalline methanol adduct, and amorphous compound.

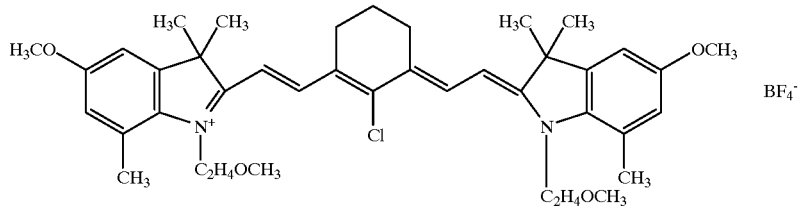

According to the method of isolation prior to purification and/or the method of purification, the above polymethine compound may assume the low-melting compound, high-melting compound, crystalline solvate or amorphous compound or a mixture of the low-melting compound, high-melting compound, crystalline solvate and amorphous compound.

The low-melting compound and high-melting compound can be respectively produced by the methods described hereinbefore. The crystalline methanol adduct can be produced by a procedure which comprises dissolving the high-melting compound, low-melting compound or amorphous compound or a mixture thereof in methanol, concentrating the solution under reduced pressure until the residue becomes 2~5 times the amount of the solid matter and filtering the same. The amorphous compound can be produced by a procedure which comprises dissolving the isolated high-melting compound, low-melting compound, crystalline methanol adduct or amorphous compound or a mixture thereof thoroughly in acetone, concentrating the solution under reduced pressure, and drying the residue.

The compound represented by the general formula (II) can be synthesized, for example, by the method described in, inter alia, JP Kokai H01-131277.

The diformyl compound represented by the general formula (III) can be synthesized, for example, by the method described in Journal of Organic Chemistry, 42, 885–888 (1977), for instance. The dianil compound represented by the general formula (IV) can be readily synthesized by reacting the diformyl compound of general formula (III) with aniline hydrochloride.

[Near infrared absorbing material]

The near infrared absorbing material of the present invention may contain a binder resin in addition to the polymethine compound of general formula (I).

The near infrared absorbing material may comprise one or more of various known near infrared absorbing materials in combination with the polymethine compound of general formula (I) within the limits beyond which the object of the present invention cannot be fulfilled.

As the known near infrared absorbers which can be used in combination, there may be mentioned carbon black, aniline black and other pigments, the various polymethine dyes (cyanine dyes), phthalocyanine dyes, dithiol metal complex dyes, naphthoquinone and anthraquinone dyes, triphenylmethane (-like) dyes, aluminum, diimmonium dyes, etc. which are described in "Kagaku Kogyo (Chemical Industry)", May, 1986, pages 45–51 under the title "Near infrared absorbing dyes" or in the monograph "Development and Market Trends of Functional Dyes for the Nineties", publsihed by CMC, 1990, Chapter 2, Paragraphs 2 and 3, and, further, azo dyes, indoaniline metal complex dyes, intermolecular CT dyes and other pigments and dyes.

The binder resin is not particularly restricted but includes, among others, homopolymers and copolymers based on acrylic acid, methacrylic acid, acrylic esters, methacrylic esters and other acrylic monomers, methylcellulose, ethylcellulose, cellulose acetate and other cellulosic polymers, polystyrene, vinyl chloride-vinyl acetate copolymers, polyvinylpyrrolidone, polyvinyl butyral, polyvinyl alcohol and other polymers and copolymers of vinyl compounds, polyesters, polyamides and other condensate polymers, butadiene-styrene copolymers and other rubber-like thermoplastic polymers, and polymers obtained by polymerization and crosslinking of epoxy compounds or other photopolymerizable compounds.

When the near infrared absorbing material of the present invention is to be applied to optical recording materials such as optical cards, such products can be manufactured by applying a solution of the near infrared absorbing material in an organic solvent to suitable substrates made of glass or plastics, for instance, by any of the various techniques so far used or explored, for example by spin coating. The resin for use in preparing said substrates is not particularly restricted but includes, among others, acrylic resins, polyethylene resins, vinyl chloride resins, vinylidene chloride resins, polycarbonate resins and the like. The solvent to be used in spin coating is not particularly restricted but includes, among others, hydrocarbons, halogenated hydrocarbons, ethers, ketones, alcohols and cellosolves and, among them, alcohols, such as methanol, ethanol and propanol, and cellosolve solvents, such as methylcellosolve and ethylcellosolve, are particularly preferred.

When the near infrared absorbing material of the present invention is to be applied to near infrared absorbing filters, infrared blocking materials or films for agricultural use, these can be produced by admixing the near infrared absorbing material with a plastic resin, if necessary together with an organic solvent, and molding the mixture into sheets or films by any of the various techniques so far explored, for example by injection molding or casting. The resin to be used is not particularly restricted but includes, among others, acrylic resins, polyethylene resins, vinyl chloride resins, vinylidene chloride resins, polycarbonate resins and the like. The solvent to be used is not particularly restricted but includes, among others, hydrocarbons, halogenated hydrocarbons, ethers, ketones, alcohols and cellosolves and, among them, alcohols, such as methanol, ethanol and propanol, and cellosolve solvents, such as methylcellosolve and ethylcellosolve, are particularly preferred.

When the near infrared absorbing material of the present invention is used in laser thermal transfer recording materials, laser heat-sensitive recording materials and like recording materials, a chromogen component or a colorant component, for instance, may be incorporated in the near infrared absorbing material, or a layer containing a chromogen component or a colorant component, for instance, may be provided separately. Usable as the chromogen or colorant component are those substances capable of forming images as the result of a physical or chemical change due to heat which have so far been explored in various ways, for example subliming dyes or pigments, electron-donating dye precursors combined with an electron-accepting compound, and polymerizable polymers. Thus, for example, the colorant component in a laser thermal transfer recording material is not particularly restricted but includes inorganic pigments such as titanium dioxide, carbon black, zinc oxide, Prussian blue, cadmium sulfide, iron oxide, and lead, zinc, barium and calcium chromates, and organic pigments such as azo, thioindigo, anthraquinone, anthanthrone, triphenodioxane, phthalocyanine, quinacridone and other type pigments. As dyes, there may be mentioned acid dyes, direct dyes, disperse dyes, oil colors, metal-containing oil colors, and so forth.

The chromogen component for use in a laser heat-sensitive recording material is not particularly restricted but may be any of those chromogens conventionally used in heat-sensitive recording materials. As the electron-donating dye precursors, namely substances capable of donating an electron or electrons and accepting a proton or protons from an acid or acids or the like to thereby develop a color, use may be made of those compounds having such a partial skeleton as a lactone, lactam, sultone, spiropyran, ester or amide structure and capable of undergoing ring opening or cleavage of such partial skeleton upon contact with an electron-accepting compound. Thus, for example, there may be mentioned triphenylmethane compounds, fluoran compounds, phenothiazine compounds, indolylphthalide compounds, lueco auramine compounds, rhodamine lactam compounds, triphenylmethane compounds, triazene compounds, spiropyran compounds and fluorene compounds, among others. As the electron-accepting compound, there may be mentioned phenolic compounds, organic acids or salts thereof, and hydroxybenzoic acid esters, among others.

[An original plate for direct plate making]

The polymethine compound of the present invention can be judiciously used as a near infrared absorbing material in original plates for direct plate making. The original plates for direct plate making comprise a light-to-heat conversion layer provided on a substrate. A silicone rubber layer and/or a protective layer may be provided on the light-to-heat conversion layer.

The components constituting the light-to-heat conversion layer include, in addition to the polymethine compound of the present invention, an image forming component, a binder resin and so forth. Alternatively, a layer containing an image forming component may be provided on the light-to-heat conversion layer.

Useful as the image forming component are those substances which can form images as the result of a physical or chemical change due to heat and which have so far been explored in various ways. Thus, for example, there may be mentioned, without any particular restriction, those containing a microencapsulated heat-fusible substance and a binder resin, among others, as disclosed in JP Kokai H03-108588, those containing a blocked isocyanate, among others, together with an active hydrogen-containing binder on a substrate having a hydrophilic surface as disclosed in JP Kokai S62-164049, those containing a microencapsulated lipophilic component and a hydrophilic binder polymer, among others, as disclosed in JP Kokai H07-1849, those containing an acid precursor, a vinyl ether group-containing compound and an alkali-soluble resin, for instance, as disclosed in JP Kokai H08-220752, those containing a hydroxy-containing macromolecular compound and an o-naphthoquinone diazide compound, among others, as disclosed in JP Kokai H09-5993, those containing nitrocellulose, among others, as disclosed in JP Kokai H09-131977, and those containing a polymerization initiator and an ethylenically unsaturated monomer, oligomer or macromonomer, among others, as disclosed in JPKokai H09-14626. Optionally, a silicone rubber layer may be laid on the light-to-heat conversion layer (photosensitive or heat-sensitive layer) so that said silicone rubber layer may be subjected to firm adhesion or peeling off after exposure to thereby form image areas, as disclosed in JP Kokai H09-80745, JP Kokai H09-131977, JP Kokai H09-146264 and elsewhere.

The binder resin to be used in the light-to-heat conversion layer is not particularly restricted but includes, among others, homopolymers or copolymers of acrylic acid, methacrylic acid, acrylic esters, methacrylic esters or like acrylic monomers, methylcellulose, ethylcellulose, cellulose acetate and like cellulosic polymers, polystyrene, vinyl chloride-vinyl acetate copolymers, polyvinylpyrrolidone, polyvinyl butyral, polyvinyl alcohol and like vinyl polymers and copolymers of vinyl compounds, polyesters, polyamides and like polycondesates, butadiene-styrene copolymers and like rubber-like thermoplastic polymers, and polymers obtained by polymerization and crosslinking of epoxy compounds or like photopolymerizable compounds.

The original plate for plate making as provided by the present invention should be flexible so that it may be set on a conventional printing press and, at the same time, it should be able to endure the pressure applied at the time of printing. Thus, as the substrate or support member to be used, there may be mentioned, among others, paper, plastic-laminated (e.g. polyethylene-, polypropylene-, or polystyrene-laminated) paper, sheets of a metal such as aluminum (inclusive of aluminum alloys), zinc or copper, films made of a plastic such as cellulose diacetate, cellulose triacetate, cellulose butyrate, polyethylene terephthalate, polyethylene, polystyrene, polypropylene, polycarbonate or polyvinyl acetal, and the like. Typical among them are coated paper, sheets of a metal such as aluminum, plastic films such as polyethylene terephthalate films, rubber sheets, and composite materials produced from such materials. Preferred are aluminum sheets, aluminum-containing alloy sheets and plastic films. The substrate has a thickness of 25 μm to 3 mm, preferably 100 μm to 500 μm.

The original plate for plate making is produced generally by dissolving or dispersing the polymethine compound, image forming component, binder resin and other necessary components in an organic solvent and applying the solution or dispersion to the substrate.

As the solvent used for said application, there may be mentioned water, alcohols such as methyl alcohol, isopropyl alcohol, isobutyl alcohol, cyclopentanol, cyclohexanol and diacetone alcohol, cellosolves such as methylcellosolve and ethylcellosolve, aromatic solvents such as toluene, xylene and chlorobenzene, esters such as ethyl acetate, butyl acetate, isoamyl acetate and methyl propionate, ketones such as acetone, methyl ethyl ketone, methyl isobutyl ketone and cyclohexanone, chlorinated hydrocarbons such as methylene chloride, chloroform and trichloroethylene, ethers such as tetrahydrofuran and dioxane, and aprotic polar solvents such as N,N-dimethylformamide and N-methylpyrrolidone.

Between the substrate and light-to-heat conversion layer, there may be provided a primer layer for the purpose of improving adhesiveness or printability, or the substrate itself may be subjected to surface treatment. Thus, for example, a layer of any of various photosensitive polymers may be cured by exposure to light prior to providing the light-to-heat conversion layer, as disclosed in JP Kokai S60-22903, a layer of an epoxy resin may be heat-cured, as disclosed in JP Kokai S62-50760, a gelatin layer may be hardened, as disclosed in JP Kokai S63-133151 and, further, a urethane resin and a silane coupling agent may be used, as disclosed in JP Kokai H03-200965, or a urethane resin may be used, as disclosed in JP Kokai H03-273248.

As regards the protective layer for surface protection of the light-to-heat conversion layer or silicone rubber layer, transparent films made of polyethylene, polypropylene, polyvinyl chloride, polyvinylidene chloride, polyvinyl alcohol, polyethylene terephthalate or cellophane, for instance, may be used for lamination. Such films may be stretched or oriented prior to application.

The original plate for direct printing plate making according to the present invention is tailored to a semiconductor laser having a certain light emission band. Thus, in order to fabricate a printing plate using the above original plate, it is irradiated with laser light using a semiconductor laser having an emission band of 750~900 nm, preferably 770~850 nm, in accordance with the known plate-making method to form image and non-image areas according to digital data from a computer or the like.

EXAMPLES

The following examples illustrate the present invention in further detail. These examples, however, are by no means limitative of the scope of the present invention.

Example 1

Polymethine compound [synthesis of compound (11)]

A compound of general formula (II) ($R_1$=methoxy, $R_2$=methoxyethyl, $R_3$=$R_4$=methyl, Y=7-methoxy, Z=$ClO_4^-$, n=1) (3.79 g), 0.86 g of a compound of general formula (III) (X=Cl) and 3.36 g of potassium acetate were added to 50 ml of acetic anhydride, and the mixture was stirred at 45~50° C. for 60 minutes and then discharged into 300 ml of a 2% aqueous solution of $KClO_4$. The resulting crystalline precipitate was collected by filtration, washed with water and recrystallized from isopropyl alcohol to give 2.95 g of the compound (11) specifically shown hereinabove.

The elemental analysis data, melting point, absorption maximum wavelength (λmax) and gram extinction coefficient (εg) of this compound were as follows:

Elemental analysis ($C_{40}H_{52}Cl_2N_2O_{10}$) MW=791.8;

|  | C | H | N |
|---|---|---|---|
| Calcd. (%) | 60.68 | 6.62 | 3.54; |
| Found (%) | 59.96 | 6.49 | 3.58. |

Melting point (° C.): 152~153° C.; λmax: 832 nm (in diacetone alcohol); εg: $2.80 \times 10^5$ ml/g·cm.

The IR spectrum of the compound obtained is shown in FIG. 1.

Figure 9:
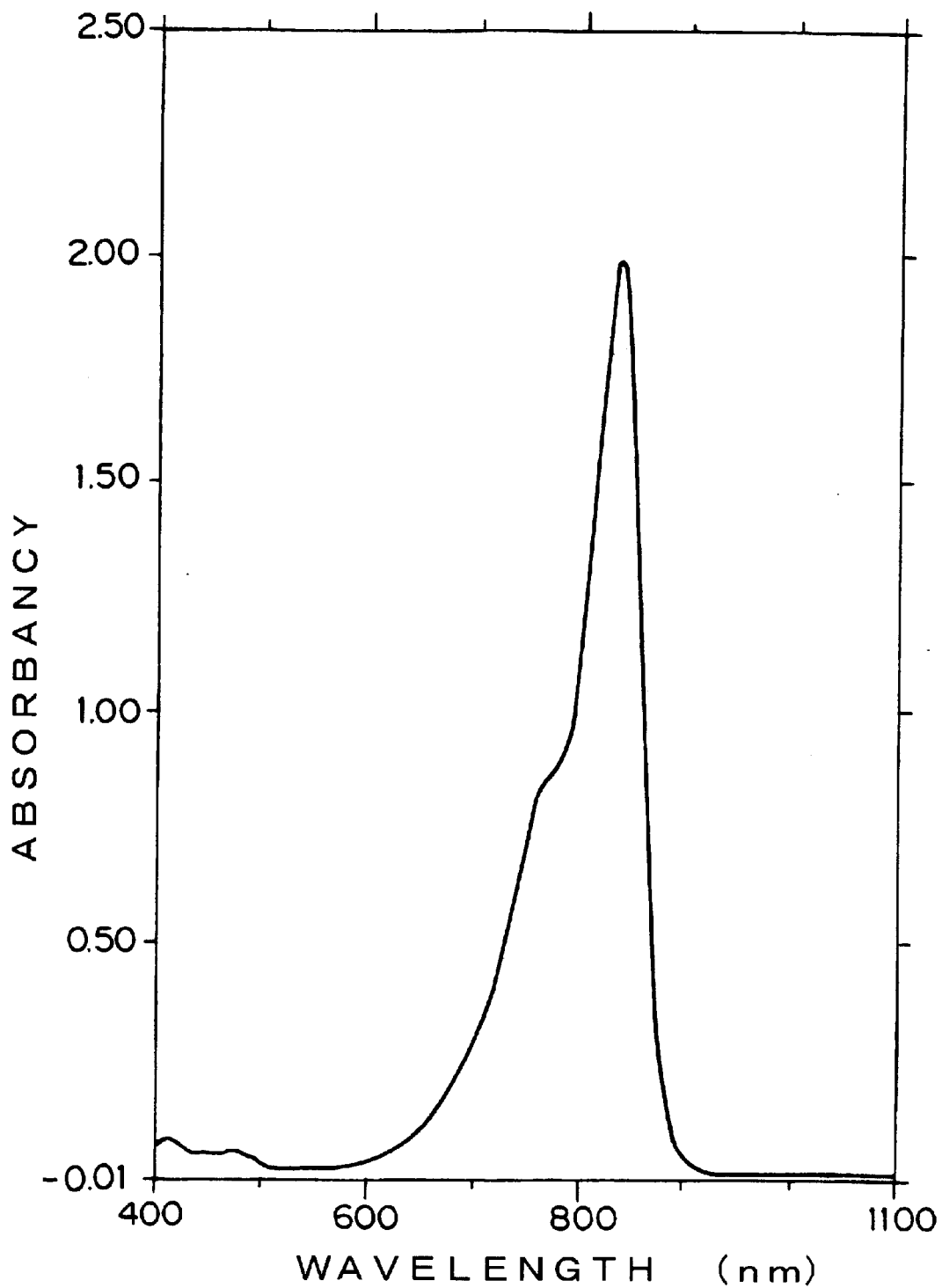
FIG. 9 is VIS-NIR absorption spectrum of the polymethine compound according to Example 1 in diacetone alcohol.

The VIS-NIR absorption spectrum of the compound obtained is shown in FIG. 9.

Example 2

Polymethine compound [synthesis of compound (12)]

A compound of general formula (II) ($R_1$=methoxy, $R_2$=methoxyethyl, $R_3$=$R_4$=methyl, Y=7-methoxy, Z=$I^-$, n=1) (4.05 g), 1.80 g of a compound of general formula (IV) (X=Cl) and 3.36 g of potassium acetate were added to 50 ml of acetic anhydride, and the mixture was stirred at 45~50° C. for 60 minutes and then discharged into 300 ml of a 2% aqueous solution of KI. The resulting crystalline precipitate was collected by filtration, washed with water and recrystallized from isopropyl alcohol to give 2.56 g of the compound (12) specifically shown hereinabove.

The elemental analysis data, melting point, absorption maximum wavelength (λmax) and gram extinction coefficient (εg) of this compound were as follows:

Elemental analysis ($C_{40}H_{52}ClIN_2O_6$): MW=819.2;

|  | C | H | N |
|---|---|---|---|
| Calcd. (%) | 58.65 | 6.40 | 3.42; |
| Found (%) | 58.36 | 6.43 | 3.32. |

Melting point (° C.): 167~168° C.; λmax: 832 nm (in diacetone alcohol); εg: $2.65 \times 10^5$ ml/g·cm.

Figure 2:
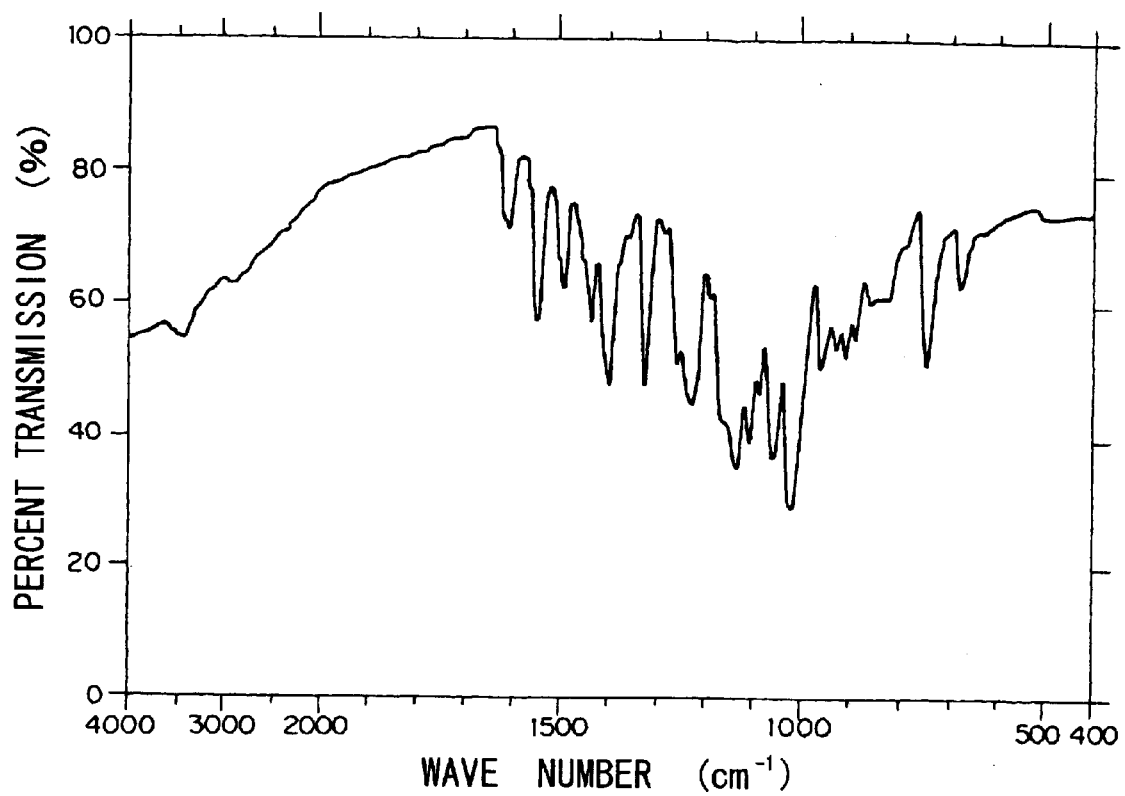
FIG. 2 is an IR absorption spectrum of the polymethine compound according to Example 2.

The IR spectrum of the compound obtained is shown in FIG. 2.

Example 3

Polymethine compound [synthesis of compound (13)]

The compound (13) specifically shown hereinabove was obtained in the same manner as in Example 1 except that 3.65 g of the corresponding compound (II) ($R_1$=methoxy, $R_2$=methoxyethyl, $R_3$=$R_4$=methyl, Y=7-methoxy, Z=$BF_4^-$, n=1) was used and that 300 ml of a 2% aqueous solution of $KBF_4$ was used in lieu of 300 ml of the 2% aqueous solution of $KClO_4$. The yield was 2.92 g.

The elemental analysis data, melting point, absorption maximum wavelength (λmax) and gram extinction coefficient (εg) of this compound were as follows:

Elemental analysis ($C_{40}H_{52}BClF_4N_2O_6$): MW=779.1;

|  | C | H | N |
|---|---|---|---|
| Calcd. (%) | 61.66 | 6.73 | 3.60; |
| Found (%) | 61.39 | 6.75 | 3.55. |

Melting point (° C.): 150~152° C.; λmax: 832 nm (in diacetone alcohol); εg: $2.85 \times 10^5$ ml/g·cm.

Figure 3:
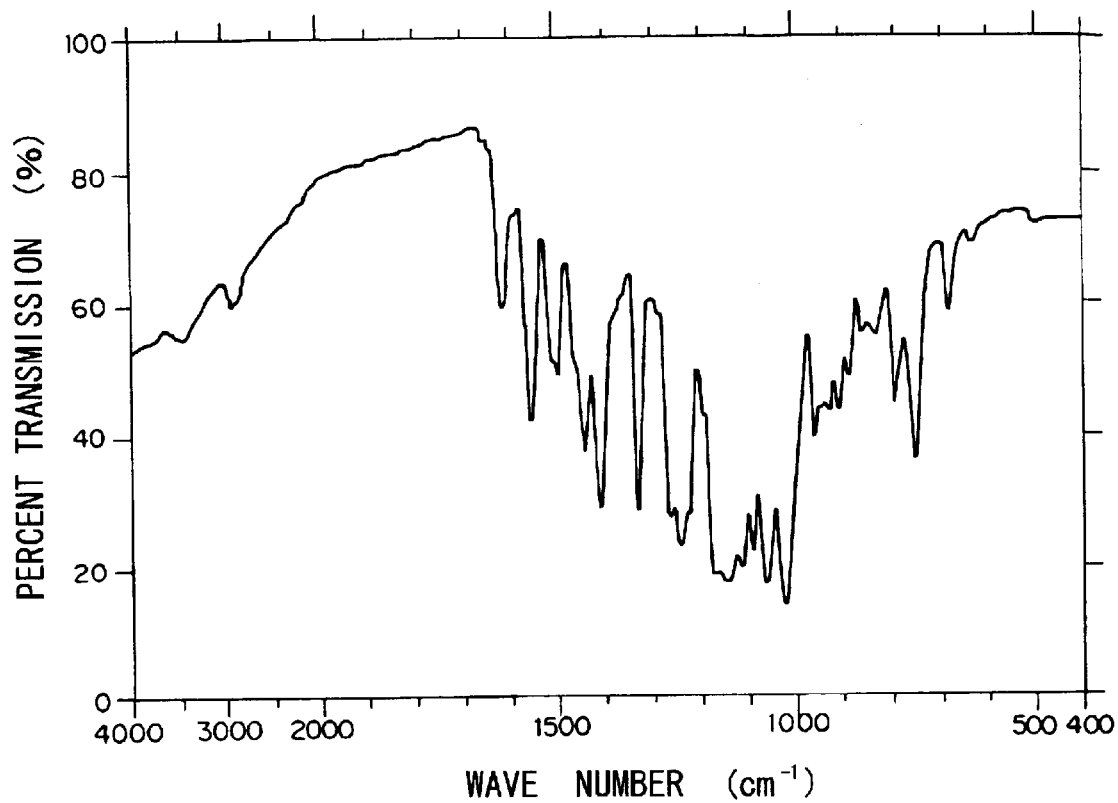
FIG. 3 is an IR absorption spectrum of the polymethine compound according to Example 3.

The IR spectrum of the compound obtained is shown in FIG. 3.

Example 4

Polymethine compound [synthesis of compound (17)]

The compound (17) specifically shown hereinabove was obtained in the same manner as in Example 1 except that 4.06 g of the compound of formula (II) (R1=methoxy, $R_2$=$R_3$=$R_4$=methyl, Y=6-methoxy, Z=p-toluenesulfonate, n=1) was used and that 300 ml of a 2% aqueous solution of p-toluenesulfonic acid was used in lieu of 300 ml of the 2% aqueous solution of $KClO_4$. The yield was 2.72 g.

The elemental analysis data, melting point, absorption maximum wavelength (λmax) and gram extinction coefficient (εg) of this compound were as follows:

Elemental analysis ($C_{43}H_{51}ClN_2O_7S$): MW=775.4;

|  | C | H | N |
|---|---|---|---|
| Calcd. (%) | 66.61 | 6.63 | 3.61; |
| Found (%) | 65.96 | 6.72 | 3.54. |

Melting point (° C.): 169~171° C.; λmax: 831 nm (in diacetone alcohol); εg: $2.60 \times 10^5$ ml/g·cm.

Figure 4:
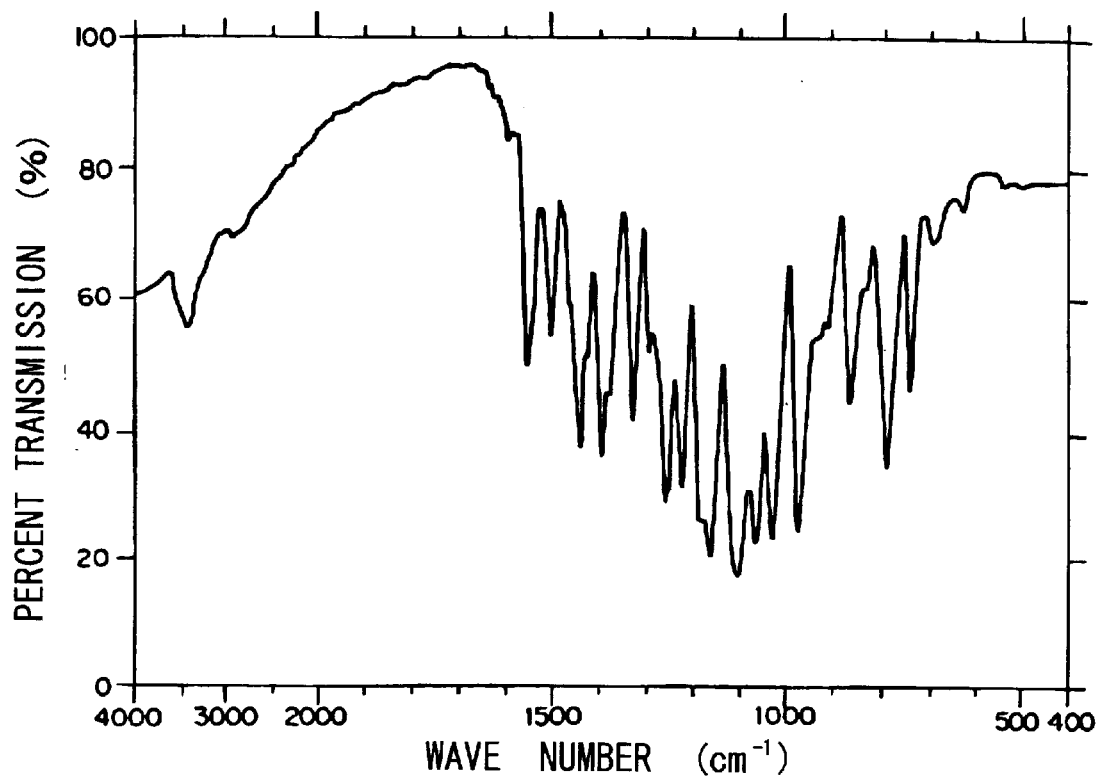
FIG. 4 is an IR absorption spectrum of the polymethine compound according to Example 4.

The IR spectrum of the compound obtained is shown in FIG. 4.

Example 5

Polymethine compound [synthesis of compound (19)]

The compound (19) specifically shown hereinabove was obtained in the same manner as in Example 2 except that 3.61 g of the corresponding compound (II) (R1=methoxy, $R_2$=methoxyethyl, $R_3$=$R_4$=methyl, Y=7-methyl, Z=$ClO_4^-$, n=1) was used and that 300 ml of a 2% aqueous solution of $KClO_4$ was used in lieu of 300 ml of the 2% aqueous solution of KI. The yield was 3.05 The elemental analysis data, melting point, absorption maximum wavelength (λmax) and gram extinction coefficient (εg) of this compound were as follows:

Elemental analysis ($C_{40}H_{52}Cl_2N_2O_8$): MW=759.8;

|  | C | H | N |
|---|---|---|---|
| Calcd. (%) | 63.23 | 6.90 | 3.69; |
| Found (%) | 62.97 | 6.85 | 3.73. |

Melting point (° C.): 197~198° C.; λmax: 822 nm (in diacetone alcohol); εg: $3.12 \times 10^5$ ml/g·cm.

Figure 5:
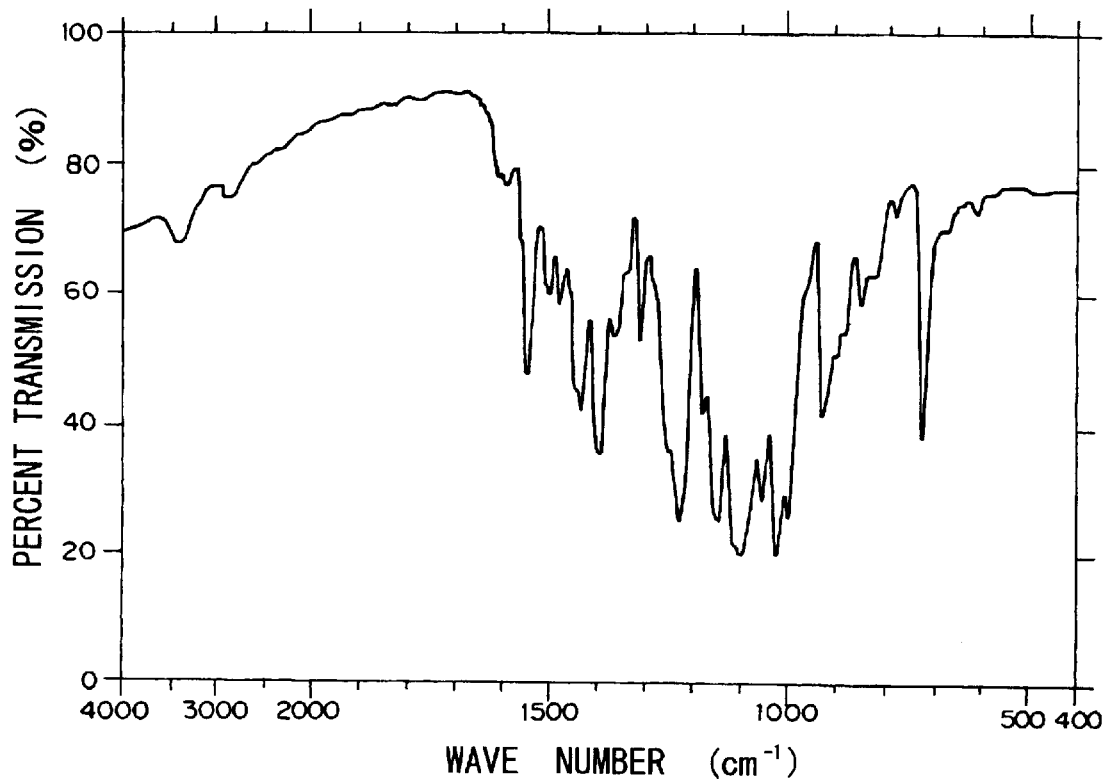
FIG. 5 is an IR absorption spectrum of the polymethine compound according to Example 5.

The IR spectrum of the compound obtained is shown in FIG. 5.

Figure 10:
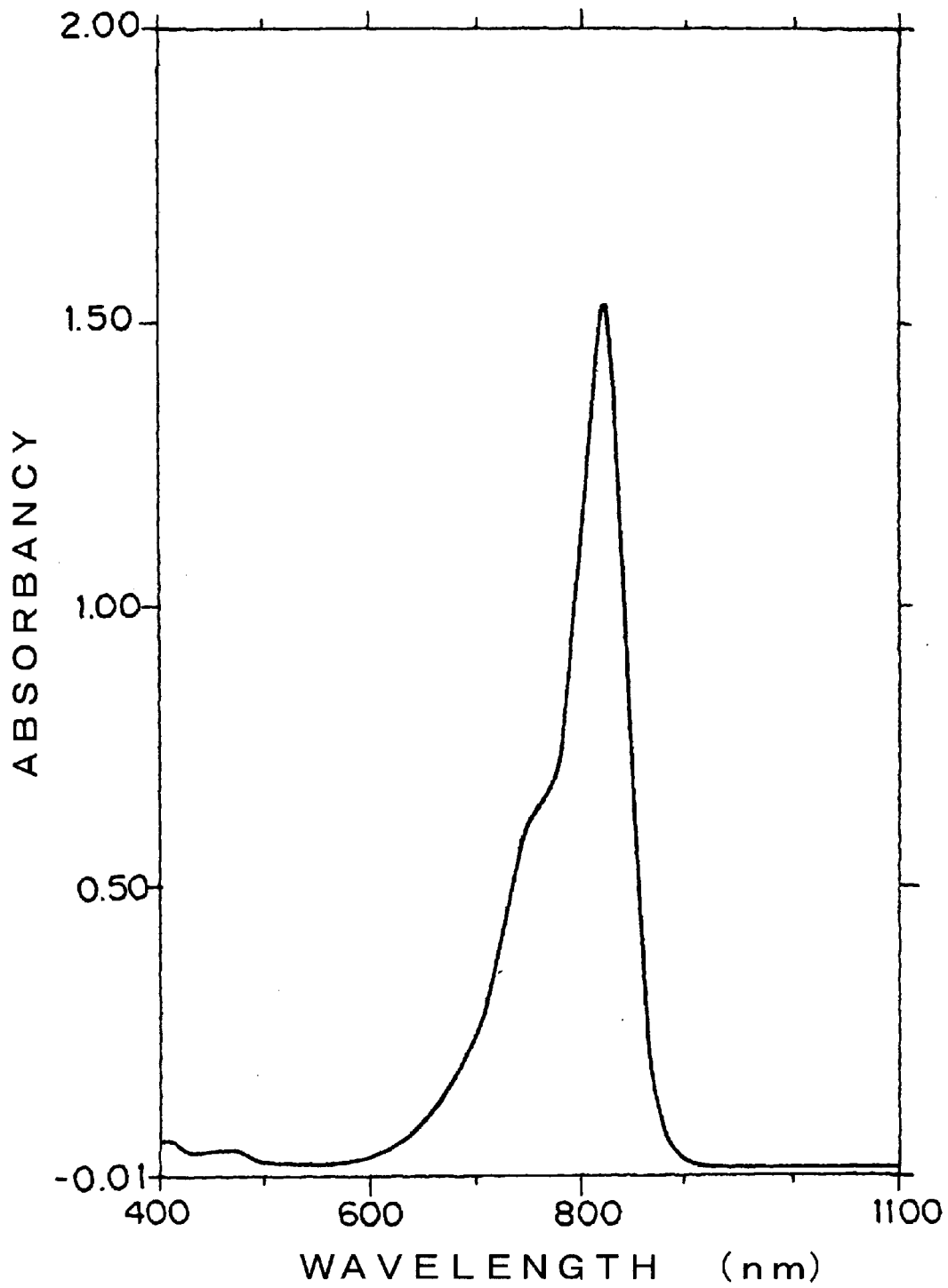
FIG. 10 is VIS-NIR absorption spectrum of the polymethine compound according to Example 5 in diacetone alcohol.

The VIS-NIR absorption spectrum of the compound obtained is shown in FIG. 10.

Example 6

Polymethine compound [synthesis of compound (47)]

The compound (47) specifically shown hereinabove was obtained in the same manner as in Example 1 except that 4.34 g of the compound of formula (II) ($R_1$=methoxy, $R_2$=methoxyethyl, $R_3$=$R_4$=methyl, Y=7-methyl, Z=p-toluenesulfonate, n=1) was used and that 300 ml of a 2% aqueous solution of p-toluenesulfonic acid was used in lieu of 300 ml of the 2% aqueous solution of $KClO_4$. The yield was 2.70 g.

The elemental analysis data, melting point, absorption maximum wavelength (λmax) and gram extinction coefficient (εg) of this compound were as follows:

Elemental analysis ($C_{47}H_{59}ClN_2O_7S$): MW=831.5;

|  | C | H | N |
|---|---|---|---|
| Calcd. (%) | 67.89 | 7.15 | 3.37; |
| Found (%) | 67.20 | 7.24 | 3.45. |

Melting point (° C.): 205~207° C.; λmax: 822 nm (in diacetone alcohol); εg: 2.80×10⁵ ml/g·cm.

Figure 6:
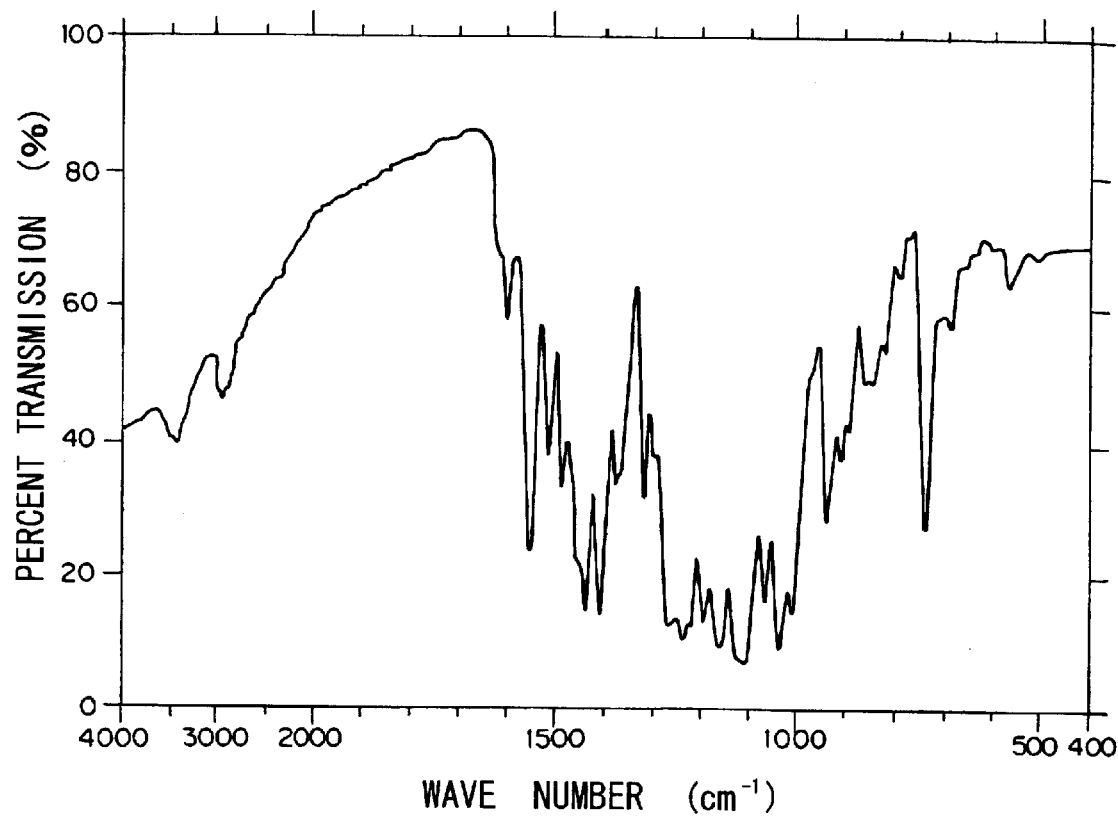
FIG. 6 is an IR absorption spectrum of the polymethine compound according to Example 6.

The IR spectrum of the compound obtained is shown in FIG. 6.

Example 7
Polymethine compound [synthesis of compound (51)]

A compound of general formula (II) ($R_1$=methoxy, $R_2$=3-sulfopropyl, $R_3$=$R_4$=methyl, Y=7-methyl, n=0) (3.25 g), 1.80 g of a compound of general formula (IV) (X=Cl) and 3.36 g of potassium acetate were added to 50 ml of acetic anhydride, and the mixture was stirred at 65~70° C. for 60 minutes. Then, 200 ml of isopropyl alcohol was added and the resulting mixture was further stirred at the same temperature for 60 minutes. After evaporation to dryness, 100 ml of ethyl acetate was added, and the mixture was stirred at room temperature for an hour. The resulting crystalline precipitate was collected by filtration, washed with 10 ml of ethyl acetate and recrystallized from 100 ml of methanol. The crystals obtained were dissolved in a solution composed of 2 g of sodium acetate, 100 ml of methanol and 100 ml of isopropyl alcohol, and the solvents were distilled off at ordinary pressure. The resulting crystalline precipitate was collected by filtration and dried to give 2.30 g of the compound (51) specifically shown hereinabove.

The elemental analysis data, absorption maximum wavelength (λmax) and gram extinction coefficient (εg) of this compound were as follows:

Elemental analysis ($C_{40}H_{50}ClN_2NaO_8S_2$): MW=809.4;

|  | C | H | N |
|---|---|---|---|
| Calcd. (%) | 59.36 | 6.23 | 3.46; |
| Found (%) | 58.69 | 6.37 | 3.37. |

Melting point (° C.): 260~261° C. (decomp.); λmax: 824 nm (in diacetone alcohol); εg: 2.82×10⁵ ml/g·cm.

Figure 7:
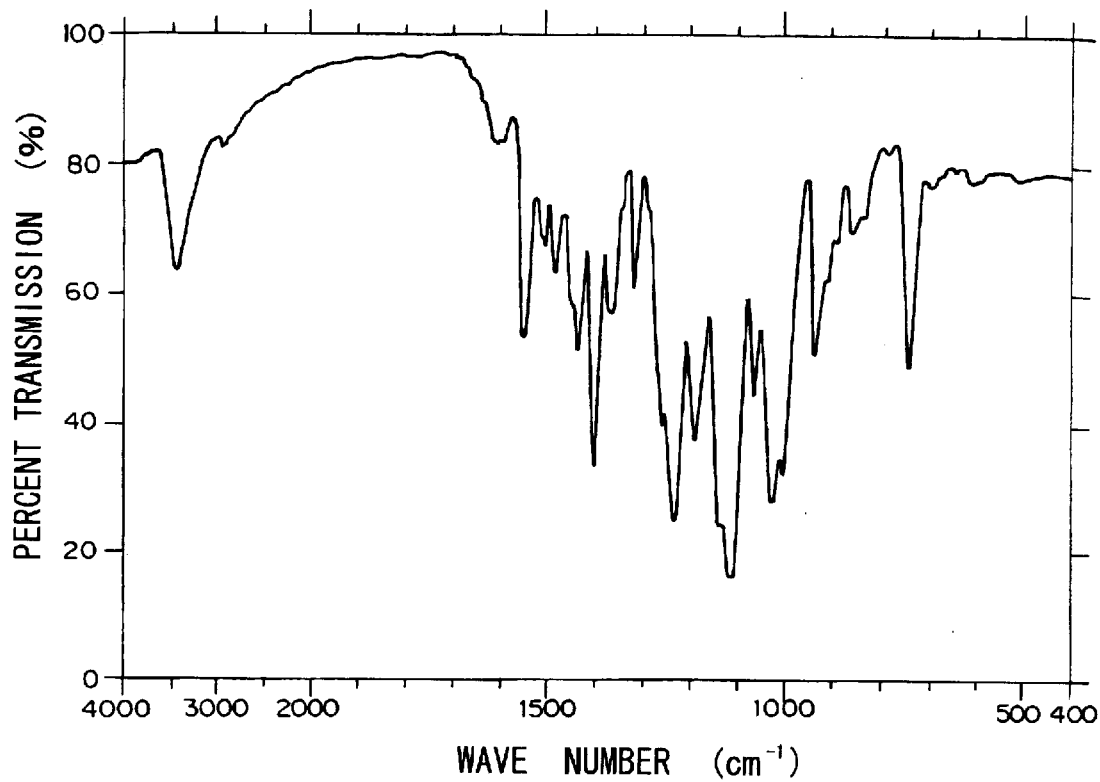
FIG. 7 is an IR absorption spectrum of the polymethine compound according to Example 7.

The IR spectrum of the compound obtained is shown in FIG. 7.

The VIS-NIR absorption spectrum of the compound obtained is shown in FIG. 11.

Example 8
Polymethine compound [synthesis of compound (55)]

The compound (55) specifically shown hereinabove was obtained in the same manner as in Example 2 except that 3.62 g of the corresponding compound (II) ($R_1$=methoxy, $R_2$=methoxyethyl, $R_3$=$R_4$=methyl, Y=7-methyl, Z=$BF_4^-$, n=1) was used and that 300 ml of a 2% aqueous solution of $KBF_4$ was used in lieu of 300 ml of the 2% aqueous solution of KI. The yield was 2.20 g.

The elemental analysis data, melting point, absorption maximum wavelength (λmax) and gram extinction coefficient (εg) of this compound were as follows:

Elemental analysis ($C_{40}H_{52}BClF_4N_2O_4$): MW=747.1;

|  | C | H | N |
|---|---|---|---|
| Calcd. (%) | 64.30 | 7.02 | 3.75; |
| Found (%) | 64.21 | 6.91 | 3.70. |

Melting point (° C.): 198~199° C.; λmax: 822 nm (in diacetone alcohol); εg: 3.20×10⁵ ml/g·cm.

The IR spectrum of the compound obtained is shown in FIG. 6.

Example 9
Polymethine compound [preparation of amorphous form of compound (55)]

The compound (55) obtained in Example 8 (2.0 g) was dissolved in 20 ml of acetone and the solution was concentrated and dried to give 1.95 g of the amorphous form of compound (55).

The elemental analysis data, melting point, absorption maximum wavelength (λmax) and gram extinction coefficient (εg) of this compound were as follows:

Elemental analysis ($C_{40}H_{52}BCF_4N_2O_4$): MW 747.1;

|  | C | H | N |
|---|---|---|---|
| Calcd. (%) | 64.30 | 7.02 | 3.75; |
| Found (%) | 64.24 | 6.99 | 3.69. |

Melting point (° C.): indefinite; λmax: 822 nm (in diacetone alcohol); εg: 3.18×20⁵ ml/g·cm.

Figure 12:
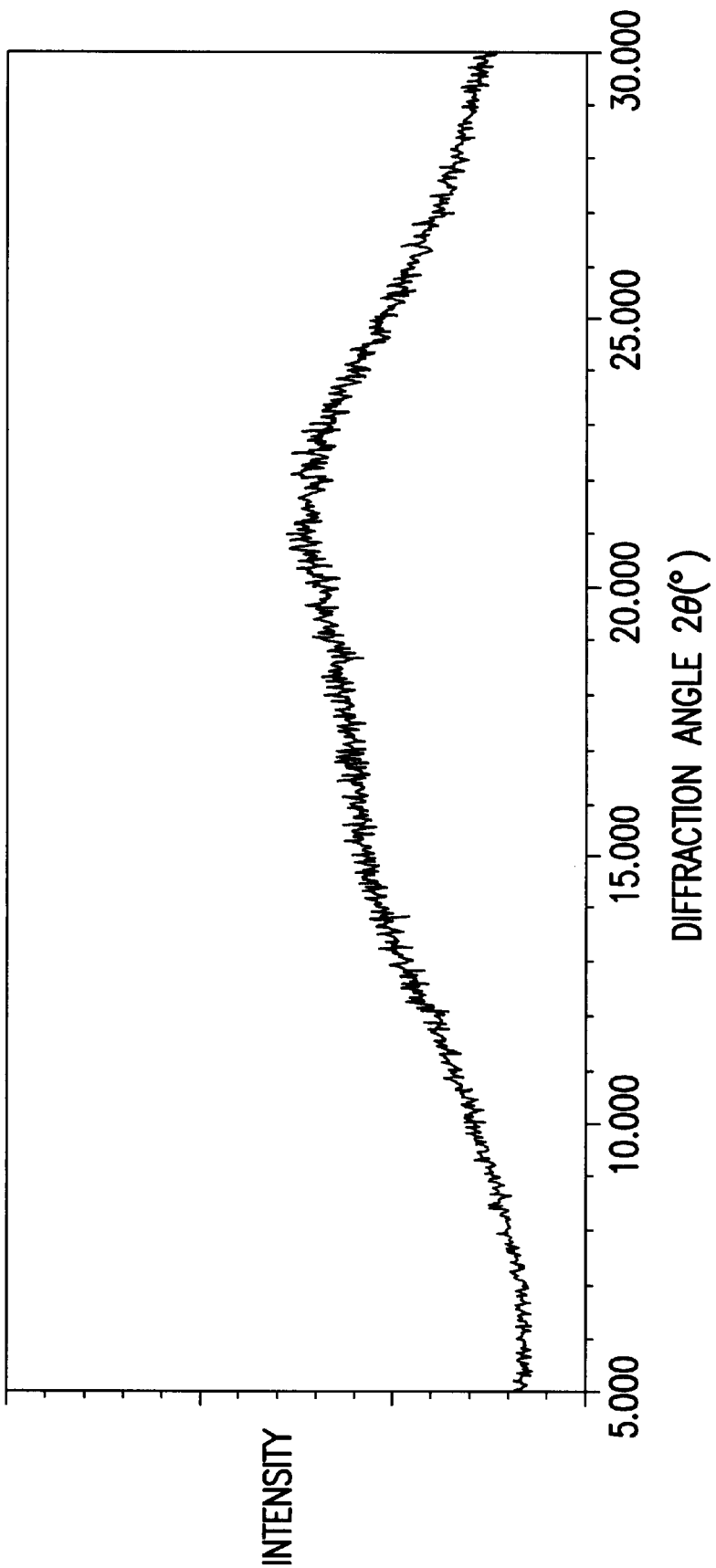
FIG. 12 is a powder X-ray diffraction pattern of the polymethine compound according to Example 9.

The powder X-ray diffraction pattern is shown in FIG. 12.

Example 10
Polymethine compound [preparation of the β-crystal form of compound (55)]

The compound (55) obtained in Example 8 (2.0 g) was recrystallized from 30 ml of methanol to give 1.42 g of the β-crystal of compound (55).

The elemental analysis data, melting point, absorption maximum wavelength (λmax) and gram extinction coefficient (εg) of this compound were as follows:

Elemental analysis ($C_{40}H_{52}BClF_4N_2O_4$): MW=747.1;

|  | C | H | N |
|---|---|---|---|
| Calcd. (%) | 64.30 | 7.02 | 3.75; |
| Found (%) | 64.25 | 6.96 | 3.71. |

Melting point (° C.): 204~206° C.; λmax: 822 nm (in diacetone alcohol); εg: 3.21×10⁵ ml/g·cm.

Figure 13:
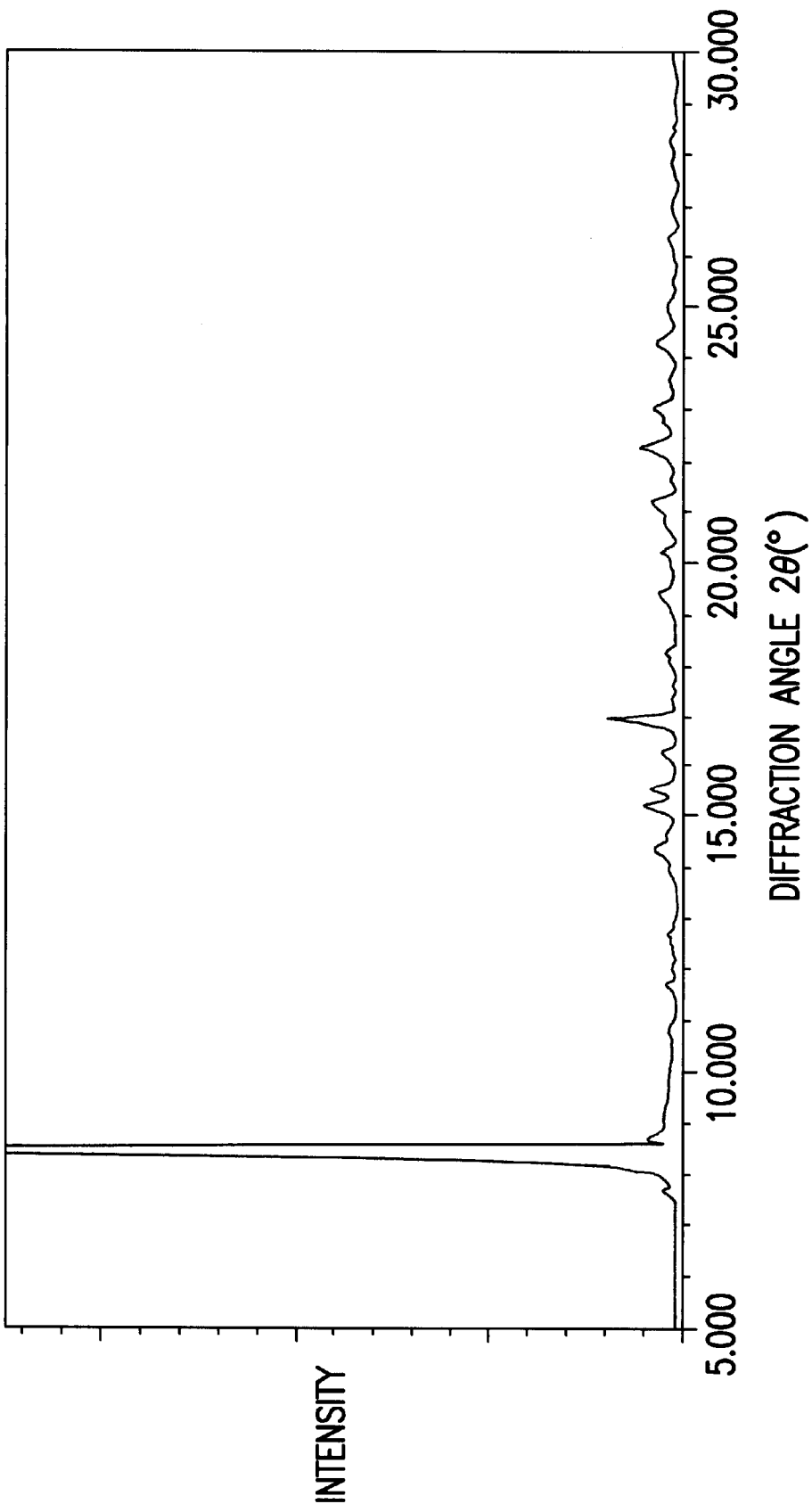
FIG. 13 is a powder X-ray diffraction pattern of the polymethine compound according to Example 10.

The powder X-ray diffraction pattern is shown in FIG. 13.

Example 11
Polymethine compound [preparation of the crystalline methanol adduct of compound (55)]

The compound (55) obtained in Example 8 (2.0 g) was dissolved in 50 ml of methanol, and using an evaporator, the solution was concentrated under reduced pressure to 7 g.

After cooling, this residue was recovered by filtration and dried to give 1.92 g of the crystalline methanol adduct of compound (55).

The melting point, absorption maximum wavelength ($\lambda$max) and gram extinction coefficient ($\epsilon$g) of this compound were as follows:

Melting point (° C.): ~180° C.; $\lambda$max: 822 nm (in diacetone alcohol); $\epsilon$g: 2.92×10⁵ ml/g·cm.

Figure 14:
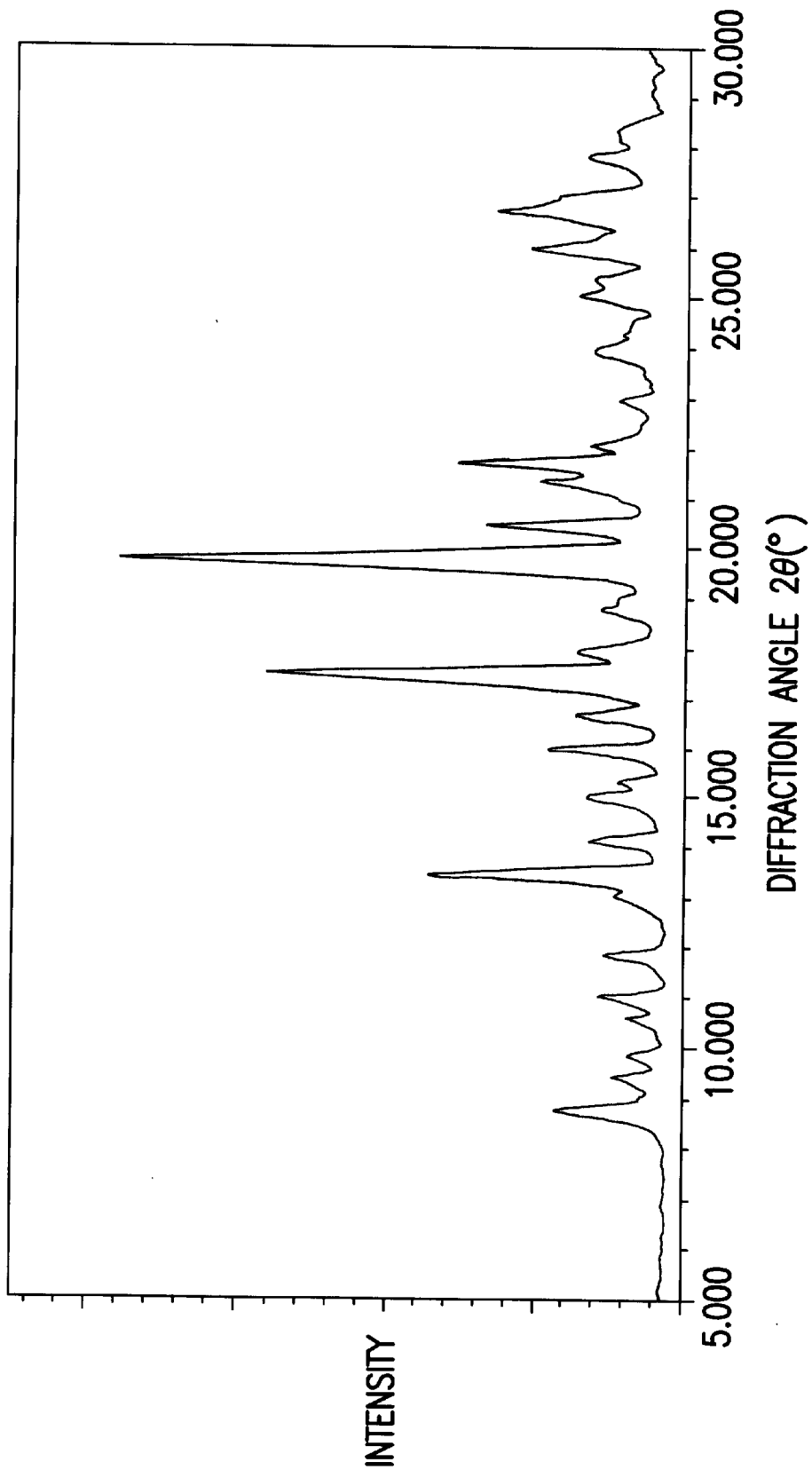
FIG. 14 is a powder X-ray diffraction pattern of the polymethine compound according to Example 11.

The powder X-ray diffraction pattern is shown in FIG. 14.

Example 12

Polymethine compound [preparation of the α-crystal form of compound (55)]

The amorphous form of compound (55) obtained in Example 9 (1.5 g) was dispersed in 20 ml of methanol at room temperature to give 1.23 g of the a-crystal of compound (55).

The elemental analysis data, melting point, absorption maximum wavelength ($\lambda$max) and gram extinction coefficient ($\epsilon$g) of this compound were as follows:

Elemental analysis ($C_{40}H_{52}BClF_4N_2O_4$): MW=747.1;

|  | C | H | N |
|---|---|---|---|
| Calcd. (%) | 64.30 | 7.02 | 3.75; |
| Found (%) | 64.21 | 6.93 | 3.71. |

Melting point (° C.): 195~197° C.; $\lambda$max: 822 nm (in diacetone alcohol); $\epsilon$g: 3.20×105 ml/g·cm.

Figure 15:
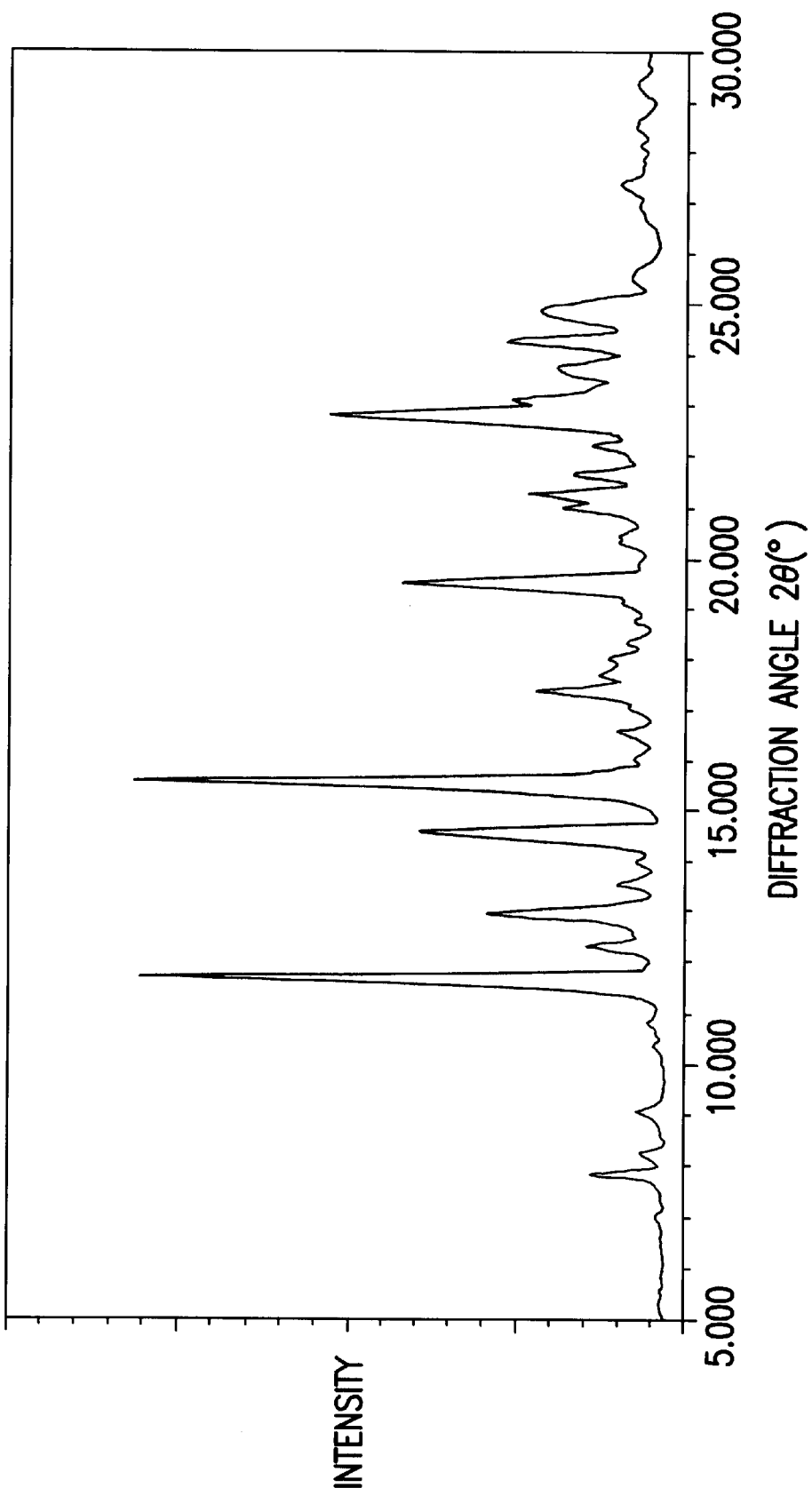
FIG. 15 is a powder X-ray diffraction pattern of the polymethine compound according to Example 12.

The powder X-ray diffraction pattern is shown in FIG. 15.

[Maximum absorption wavelength]

The maximum absorption wavelength ($\lambda$max) of the polymethine compound of the present invention in diacetone alcohol as well as those of known Compound A and Compound B were measured. The results are shown in Table 1.

TABLE 1

|  | $\lambda$max |
|---|---|
| Compound (11) | 832 nm |
| Compound (12) | 832 nm |
| Compound (13) | 832 nm |
| Compound (17) | 831 nm |
| Compound (19) | 822 nm |
| Compound (47) | 822 nm |
| Compound (51) | 824 nm |
| Compound (55) | 822 nm |
| Compound A | 788 nm |
| Compound B | 812 nm |

[Solubility Test]

The solubility of the polymethine compound of the invention in methyl ethyl ketone as well as the solubilities of said known Compound A and Compound B were measured. Solubility measurements were carried out by the following method.

Method:

A 5 ml screw tube was charged with 200 mg of each polymethine compound and 1 ml of methyl ethyl ketone and agitated for dissolution with Mix-Rotor at 25° C. overnight. Each sample was visually inspected for insoluble matter. When no insoluble residue was found, the solubility was rated ≧20%. When an insoluble residue was found, the solubility was rated less than 20%.

Except that each polymethine compound was used in the amounts of 150 mg, 100 mg, 50 mg, 30 mg and 10 mg instead of 200 mg, the above procedure was repeated and solubility measurements were made in the same manner. The results are shown in Table 2.

TABLE 2

|  | Solubility (g/ml) |
|---|---|
| Compound (11) | ≧20% |
| Compound (12) | ≧10%, ≧15% |
| Compound (13) | ≧20% |
| Compound (19) | ≧20% |
| Compound (47) | ≧20% |
| Compound (55) | ≧20% |
| Compound A | ≧3%, ≧5% |
| Compound B | ≧1%, ≧3% |

As the compound (55) in Tables 1 and 2, the compound synthesized in Example 8 was used for measurement.

Example 13

Production of a Near Infrared Absorbing Material

A sample was produced by applying, to a polyethylene terephthalate (PET) film having an average thickness of 5 μm, a solution of 10 g of Delpet SON (acrylic resin; product of Asahi Chemical Industry; as a binder) and 0.2 g of the above compound (11) in 90 g of a toluene-methyl ethyl ketone (1/1) mixture using a wire bar to give a dry film thickness of about 5 μm.

Laser beams from a single mode semiconductor laser (wavelength: 830 nm) were converged by means of a lens so that a beam diameter of 10 μm might be attained on the surface of said sample. The semiconductor was adjusted so that the power of the laser beam arriving at said surface might be varied within the range of 50 to 200 mW. The sample was thus irradiated with a single pulse at a pulse width of 20 μs. After completion of the irradiation, the sample was observed under the light microscope. When the laser power arriving at the surface was 50 mW, through hole formation with a diameter of about 10 μm was confirmed.

Example 14

Production of a Near Infrared absorbing Material

The procedure of Example 13 was followed in the same manner except that 0.2 g of the compound (19) was used in lieu of 0.2 g of the compound (11). The sample after completion of the irradiation was examined under an optical microscope, whereupon through hole formation with a diameter of about 10 μm was confirmed when the laser power arriving at the surface was 50 mW.

Example 15

Making of an Original Plate for direct Printing Plate Making (Formation of an undercoat layer)

On a polyethylene terephthalate film having a thickness of 175 μm, there was formed a gelatin layer as a primer layer so that the dry film thickness of said gelatin layer amounted to 0.2 μm.

(Formation of a light-to-heat conversion layer)

A light-to-heat conversion layer was formed by applying a coating composition prepared in accordance with the recipe given below to the above gelatin-coated polyethylene terephthalate film to a dry film thickness of 2 μm.

| Compound No. (11) | 0.1 weight part |
| Crisvon 3006LV (polyurethane; Product of Dainippon Ink and Chemicals) | 5.0 weight parts |
| Solsperse S27000 (product of ICI) | 0.4 weight part |

-continued

| | |
|---|---|
| Nitrocellulose (containing 30% of n-propanol) | 4.2 weight parts |
| Xylylenediamine (1 mole)-glycidyl methacrylate (4 moles) adduct | 2.0 weight parts |
| Ethyl Michler's ketone | 0.2 weight part |
| Tetrahydrofuran | 90 weight parts |
| (Formation of a silicone rubber layer) | |

A silicone rubber layer was formed on the above light-to-heat conversion layer by applying thereto a coating composition prepared in accordance with the recipe given below to a dry film thickness of 2 μm.

| | |
|---|---|
| α,ω-Divinylpolydimethylsiloxane (degree of polymerization: ca 700) | 9.0 weight parts |
| (CH$_3$)$_3$Si—O—(SiH(CH$_3$)—O)$_8$—Si(CH$_3$)$_3$ | 0.6 weight part |
| Polydimethylsiloxane (degree of polymerization: ca 8,000) | 0.5 weight part |
| Olefin-chloroplatinic acid | 0.08 weight part |
| Inhibitor HC≡C—C(CH$_3$)$_2$—O—Si(CH$_3$)$_3$ | 0.07 weight part |
| Isopar-G (product of Esso Chemical) | 55 weight parts |

Writing was made on the plate obtained in the above manner, using a semiconductor laser with an oscillation wavelength of 830 nm and a beam diameter of 10 μm. The power on the plate was 110 mW. A printing plate with sharp edges could be produced; the laser recording sensitivity was 200 mJ/cm$^2$ and the resolution was 8 μm.

Example 16
Making of an Original Plate for Direct Printing Plate Making

A plate for direct printing plate making was produced in the same manner as in Example 11 except that, in Example 15, 0.1 weight part of the compound (47) was used in lieu of 0.1 weight part of the compound (11).

Writing was made on the plate obtained in the above manner, using a semiconductor laser with an oscillation wavelength of 830 nm and a beam diameter of 10 μm. The power on the plate was 110 mW. A printing plate with sharp edges could be produced; the laser recording sensitivity was 200 mJ/cm$^2$ and the resolution was 8 μm.

Example 17
Making of an Original Plate for Direct Printing Plate Making

A plate for direct printing plating making was manufactured in the same manner as Example 11 except that, in Example 15, 0.1 weight part of the compound (55) in Table 1 was used in lieu of 0.1 weight part of the compound (11).

Writing was made on the plate obtained in the above manner, using a semiconductor laser with an oscillation wavelength of 830 nm and a beam diameter of 10 μm. The power on the plate was 110 mW. A printing plate with sharp edges could be produced; the laser recording sensitivity was 200 mJ/cm$^2$ and the resolution was 8 μm.

Comparative Example 1

The procedure of Example 13 was repeated except that 0.2 g of the polymethine compound having the structural formula shown below, which is described in JP Kokai S63-319191, was used in lieu of 0.2 g of the compound (11). In a light microscopic examination of the sample after completion of the irradiation, no through hole formation was observed even when the laser power arriving at the surface was 100 mW.

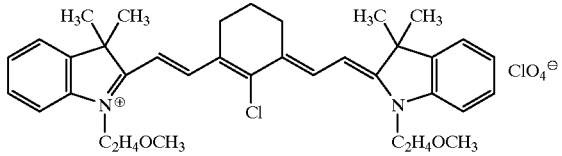

Compound A

Comparative Example 2

Except that, in Example 13, 0.2 g of the polymethine compound of the following chemical formula as described in Journal of Organic Chemistry, 60, 2392, Table 1 was used in lieu of 0.2 g of the compound (11), the procedure described in Example 13 was repeated. In a light microscopic examination of the sample after completion of the irradiation, no through hole formation was observed even when the laser power arriving at the surface was 50 mW.

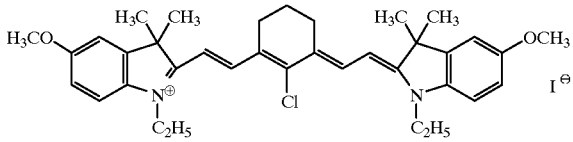

Compound B

EFFECTS OF THE INVENTION

The polymethine compound of general formula (I) shows less absorption in the visible region, and the near infrared absorbing material comprising this compound can be used with advantage in laser thermal transfer recording materials and laser heat-sensitive recording materials having good sensitivity to laser light with a high light-to-heat conversion efficiency and, therefore, enabling high-speed recording for high-density, high-quality records. The polymethine compound of general formula (I) is quite highly soluble in various solvents used for making the light-to-heat conversion layer of original plates for direct printing plate making and has good compatibility with various binder resins and other components, facilitating preparation of coating compositions. It can thus form uniform light-to-heat conversion layers and is particularly suited for use in the manufacture of original plates for direct printing plate making.

What is claimed is:
1. A polymethine compound of the following general formula

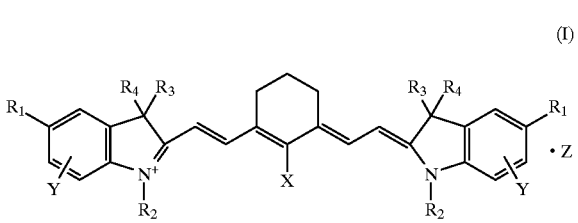

(I)

wherein R$_1$ represents an alkoxy group which may be substituted; R$_2$ represents an alkyl group which may be substituted; R$_3$ and R$_4$ each represents a lower alkyl group or R₃ and R₄ may combinedly form a cyclic structure; X represents a hydrogen atom, a halogen atom or a substituted amino group; Y represents an alkoxy group which may be substituted or an alkyl group which may be substituted; Z represents a charge neutralizing ion.

2. A polymethine compound as claimed in claim 1 wherein $R_1$ is an alkoxy group containing 1~4 carbon atoms, $R_2$ is an alkyl group containing 1~8 carbon atoms, an alkoxyalkyl group containing a total of 1~8 carbon atoms, a sulfoalkyl group containing 1~8 carbon atoms or a carboxyalkyl group containing a total of 2~9 carbon atoms, and Y is an alkoxy group containing 1~4 carbon atoms or an alkyl group containing 1~4 carbon atoms.

3. A polymethine compound as claimed in claim 1 wherein Z is $Cl^-$, $Br^-$, $I^-$, $ClO_4^-$, $BF_4^-$, $CF_3CO_2^-$, $PF_6^-$, $SbF_6^-$, $CH_3SO_3^-$, p-toluenesulfonate, $Na^+$, $K^+$ or triethylammonium ion.

4. A polymethine compound as claimed in claim 1 wherein R₃ and R₄ each is methyl or R₃ and R₄ taken together is a cyclopentane ring or a cyclohexane ring.

5. A polymethine compound as claimed in claim 1 wherein X is H, Cl, Br or diphenylamino.

6. A polymethine compound as claimed in claim 1 which is a low-melting crystal modification of 2-(2-{2-chloro-3-[(1,3-dihydro-3,3,7-trimethyl-5-methoxy-1-methoxyethyl-2H-indol-2-ylidene)ethylidene]-1-cyclohexen-1-yl}ethenyl)-3,3,7-trimethyl-5-methoxy-1-methoxyethylindolium=tetrafluoroborate having the following formula and showing a powder X-ray diffraction pattern with characteristic peaks at the diffraction angles (2θ±0.2°) of 11.6°, 14.6°, 15.6°, 19.6° and 22.9° in Cu—Kα powder X-ray diffractometry

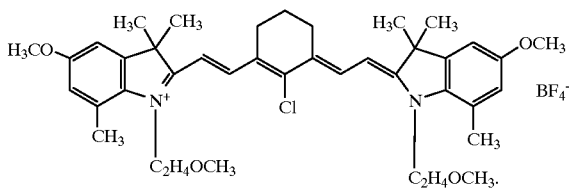

7. A polymethine compound as claimed in claim 1 which is a high-melting crystal modification of 2-(2-{2-chloro-3-[(1,3-dihydro-3,3,7-trimethyl-5-methoxy-1-methoxyethyl-2H-indol-2-ylidene)ethylidene]-1-cyclohexen-1-yl}ethenyl)-3,3,7-trimethyl-5-methoxy-1-methoxyethylindolium=tetrafluoroborate having the following formula and showing a powder X-ray diffraction pattern with a characteristic high-intensity peak at the diffraction angle (2θ±0.2°) of 8.4° in Cu—Kα powder X-ray diffractometry

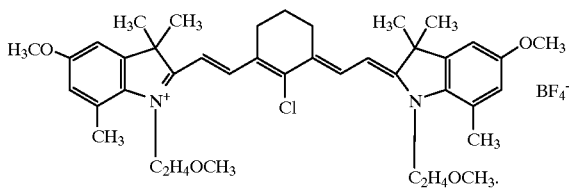

8. A polymethine compound as claimed in claim 1 which is a crystalline methanol adduct of 2-( 2-{2-chloro-3-[(1,3-dihydro-3,3,7-trimethyl-5-methoxy-1-methoxyethyl-2H-indol-2-ylidene)ethylidene]-1-cyclohexen-1-yl}ethenyl)-3,3,7-trimethyl-5-methoxy-1-methoxyethyl-indolium=tetrafluoroborate having the following formula and showing a powder X-ray diffraction pattern with characteristic peaks at the diffraction angles (2θ±0.2°) of 13.3°, 17.4°, 19.8°, 21.8° and 26.9° in Cu—Kα powder X-ray diffractometry

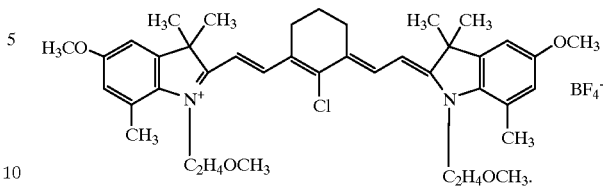

9. A polymethine compound as claimed in claim 1 which is an amorphous form of 2-(2-{2-chloro-3-[(1,3-dihydro-3,3,7-trimethyl-5-methoxy-1-methoxyethyl-2H-indol-2-ylidene)ethylidene]-1-cyclohexen-1-yl}ethenyl)-3,3,7-trimethyl-5-methoxy-1-methoxyethylindolium=tetrafluoroborate having the following formula and showing a powder X-ray diffraction pattern having no characteristic peak at the diffraction angle (2θ±0.2°) in Cu—Kα powder X-ray diffractometry

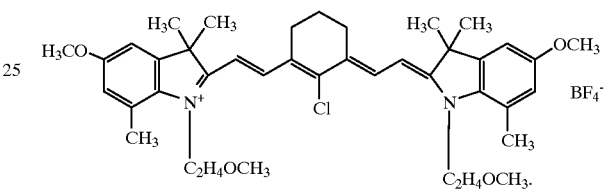

10. A process for producing the polymethine compound of claim 1 which comprises subjecting an indolenium compound of the following general formula (II) and either a diformyl compound of the following formula (III) or a dianil compound of the following formula (IV) to condensation reaction in a dehydrating organic acid in the presence of a fatty acid salt

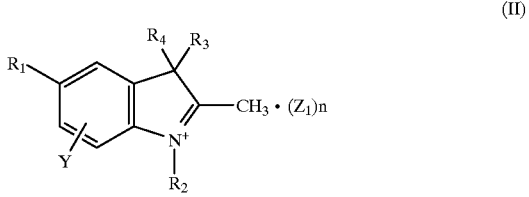

(II)

wherein $R_1$ represents an alkoxy group which may be substituted; $R_2$ represents an alkyl group which may be substituted; $R_3$ and $R_4$ each represents a lower alkyl group or $R_3$ and $R_4$ taken together represent a ring; Y represents an alkoxy group which may be substituted or an alkyl group which may be substituted; $Z_1$ represents a charge neutralizing ion; n represents a number of 0 or 1

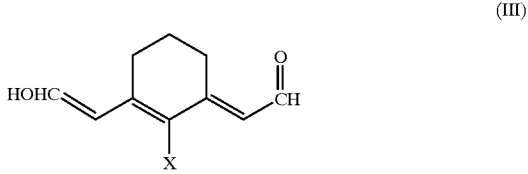

(III)

wherein X represents a hydrogen atom, a halogen atom or a substituted amino group

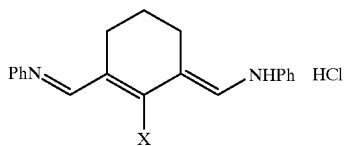 (IV)

wherein X represents a hydrogen atom, a halogen atom or a substituted amino group.

11. A process for producing low-melting crystals of the polymethine compound of claim 1 which comprises treating a crystalline solvent adduct or amorphous form of the polymethine compound of claim 1 with a solvent.

12. A process for producing high-melting crystals of the polymethine compound of claim 1 which comprises recrystallizing the polymethine compound of claim 1 from a ketonic or alcoholic solvent.

13. A near infrared absorbing material comprising the polymethine compound claimed in claim 1.

14. An original plate for direct printing plate making which comprises the polymethine compound of claim 1 in a light-to-heat conversion layer constructed on a substrate.

15. A method of manufacturing a printing plate which comprises irradiating the original plate for direct printing plate making claimed in claim 14 with light using a semiconductor laser having a light emission band of 750 nm~900 nm as a light source.

* * * * *